(12) United States Patent
Abadir et al.

(10) Patent No.: US 10,835,516 B2
(45) Date of Patent: Nov. 17, 2020

(54) PROTECTIVE, ANTI-INFLAMMATORY RECEPTOR AND ITS USE IN PRESERVATION OF MITOCHONDRIAL FUNCTION, WOUND HEALING AND REPAIR

(71) Applicant: The Johns Hopkins University, Baltimore, MD (US)

(72) Inventors: Peter M. Abadir, Woodstock, MD (US); Jeremy D. Walston, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/598,105

(22) Filed: Jan. 15, 2015

(65) Prior Publication Data
US 2015/0238465 A1 Aug. 27, 2015

Related U.S. Application Data

(62) Division of application No. 14/008,585, filed as application No. PCT/US2012/031406 on Mar. 30, 2012, now abandoned.

(60) Provisional application No. 61/490,312, filed on May 26, 2011, provisional application No. 61/469,421, filed on Mar. 30, 2011.

(51) Int. Cl.
| | | |
|---|---|---|
| *A61K 31/4178* | (2006.01) | |
| *G01N 33/566* | (2006.01) | |
| *A61K 31/41* | (2006.01) | |
| *A61K 31/4184* | (2006.01) | |
| *C07K 14/705* | (2006.01) | |
| *A61K 9/00* | (2006.01) | |

(52) U.S. Cl.
CPC ........ *A61K 31/4178* (2013.01); *A61K 9/0014* (2013.01); *A61K 31/41* (2013.01); *A61K 31/4184* (2013.01); *C07K 14/705* (2013.01); *G01N 33/566* (2013.01)

(58) Field of Classification Search
USPC ........................................................ 514/381
See application file for complete search history.

(56) References Cited

U.S. PATENT DOCUMENTS

| | | |
|---|---|---|
| 4,942,031 A | 7/1990 | Levin |
| 5,660,813 A | 8/1997 | Kon et al. |
| 2002/0187939 A1 | 12/2002 | Montgomery et al. |
| 2004/0092563 A1 | 5/2004 | Schrader |
| 2006/0135422 A1 | 6/2006 | Moskowitz |
| 2009/0143458 A1 | 6/2009 | Jensen et al. |
| 2014/0057955 A1 | 2/2014 | Abadir et al. |

FOREIGN PATENT DOCUMENTS

WO  WO-2006/078606 A2  7/2006

OTHER PUBLICATIONS

Steckelings (Differential expression of angiotensin receptors in human cutaneous wound healing, Cutaneous Biology, 2005, pp. 887-893).*
Terrie (Acne Treatments, 2008, https://www.pharmacytimes.com/publications/issue/2008/2008-12/2008-12/9940).*
Yahata (A Novel Function of Angiotensin II in Skin Wound Healing, The Journal of Biological Chemistry vol. 281, No. 19, pp. 13209-13216, May 12, 2006).*
Brem (Cellular and molecular basis of wound healing in diabetes, The Journal of Clinical Investigation http://www.jci.org, vol. 117, No. 5, May 2007.*
Abadir, P et al., "Identification and characterization of a functional mitochondrial angiotensin system." PNAS, 108(36):14849-54 (2011).
Basso, N., et al. "Protective effect of the inhibition of the renin-angiotensin system on aging," Regulatory Peptides 128 (3): 247-252 (2005).
Benigni et al., "Disruption of the Ang II type 1 receptor promotes longevity in mice." J Clin Invest. 119(3):524-30 (2009).
Cavanagh et al. "Cost of treating diabetic foot ulcers in five different countries," Diabetes Metab Res Rev. 28 Suppl 1:107-11 (2012).
Chow et al. "Management and Prevention of Diabetic Foot Ulcers and Infections: a Health Economic Review," Pharmacoeconomics, 26(12): 1019-35 (2008).
De Cavanagh, et al. "Angiotensin II blockade improves mitochondrial function in spontaneously hypertensive rats," Cellul. Mol. Biol. 51(6): 573-578 (2005).
De Cavanagh et al. "Renal mitochondrial impairment is attenuated by AT1 blockade in experimental Type I diabetes," Am. J. .Physiol. Heart and Circ. Physiol. 294(1): H456-H465 (2008).
Doughan, A.K., et al. Molecular Mechanisms of Angiotensin II-Mediated Mitochondrial Dysfunction: Linking Mitochondrial Oxidative Damage and Vascular Endothelial Dysfunction, Circ. Res. 102(4): 488-496 (2008).
Dougherty et al. "An Evidence-Based Model Comparing the Cost-effectiveness of Platelet-Rich Plasma Gel to Alternative Therapies for Patients with Nonhealing Diabetic Foot Ulcers." Adv Skin Wound Care, 21(12): 568-75 (2008).
Edwards et al. "Gold in the ivory tower: equity rewards of out licensing," Nat Biotechnol. 24(5): 509-15. (May 2006).

(Continued)

*Primary Examiner* — Kathrien A Cruz
(74) *Attorney, Agent, or Firm* — Tarolli, Sundheim, Covell & Tummino LLP

(57) ABSTRACT

Provided herein is a novel mitochondrial Angiotensin II type 1 and type 2 $AT_1R$ and $AT_2R$ receptor which plays a role in protection of mitochondria against oxidative damage. Evidence from animal studies indicates a role for this receptor in preservation of mitochondria and up-regulation of survival genes, anti-inflammatory action, and improvement of wound healing in the skin and soft tissues. Pharmaceutical compositions for treatment directed to preserving mitochondrial function, anti-inflammation, wound healing and decreasing the signs of aging, as well as medicaments and their use are also provided.

10 Claims, 26 Drawing Sheets

(56) References Cited

OTHER PUBLICATIONS

Fife et al. "Wound Care Outcomes and Associated Cost Among Patients Treated in US Outpatient Wound Centers," Data From the US Wound Registry. Wounds, 24(1): 10-7 (Jan. 2012).
Liu et al., "Angiotensin II regulates phosphoinositide 3 kinase/Akt cascade via a negative crosstalk between AT1 and AT2 receptors in skin fibroblasts of human hypertrophic scars." Life Sci, 79:475-83 (2006).
Markova, Alina, et al. "US Skin Disease Assessment: Ulcer and Wound Care," Dermatol Clin. 30(1): 107-11 (Jan. 2012).
Mavromoustakos et al., "AT1 antagonists: a patent review (2008-2012)." Expert Opin, Ther. Patents, 23(11): (2013).
Mazzocchi, G., et al. "Investigations on the Turnover of Adrenocortical Mitochondria. XV. A Stereological Study of the Effect of Chronic Treatment with Angiotensin II on the Size and Number of the Mitochondria in the Zona Glomerulosa of the Rat," Cell Tissue Res, 210: 333-337 (1980).
Naito et al., "High ambient glucose augments angiotensin II-induced proinflammatory gene mRNA expression in human mesangial cells: effects of valsartan and simvastatin." Am J Nephrol, 30:99-111 (2009).
Nakagiri et al., "Angiotensin AT1 receptor blockers suppress ischemia/reperfusion-induced gastric injury in rats." Inflammopharmacology, 15:171-174 (2007).
Romanelli, Marco, et al. "Randomized Comparison of OASIS Wound Matrix versus Moist Wound Dressing in the Treatment of Difficult-to-Heal Wounds of Mixed Arterial/Venous Etiology," Adv Skin Wound Care, 23(1):34-8 (Jan. 2010).
Shishido et al., "Suppressive effects of valsartan on microalbuminuria and CRP in patients with metabolic syndrome (val-mets)." Clin Exp Hypertens, 33(2):117-23 (2011).
Sun et al., "Tissue angiotensin II in the regulation of inflammatory and fibrogenic components of repair in the rat heart." J Lab Clin Med, 143(1):41-51 (2004).
Takeda et al., "Effects of angiotensin II receptor signaling during skin wound healing." Am J Pathol, 165(5): (2004).
Waugh, Helen V., et al. "Modeling the effects of treating diabetic wounds with engineered skin substitutes," Wound Repair Regen. 15(4): 556-65 (Jul.-Aug. 2007).
Yahata et al., "A novel function of angiotensin II in skin wound healing." J Biol Chem, 281(19):13209-16 (2006).
Yang et al., "Valsartan preconditioning protects against myocardial ischemia-reperfusion injury through TLR4/NF-kB signaling pathway." Mol Cell Biochem 330:39-46 (2009).

\* cited by examiner

PROTECTIVE, ANTI-INFLAMMATORY RECEPTOR AND ITS USE IN PRESERVATION OF MITOCHONDRIAL FUNCTION, WOUND HEALING AND REPAIR

REFERENCE TO RELATED APPLICATIONS

This application is a divisional application of U.S. application Ser. No. 14/008,585, filed Sep. 30, 2013, which is a 35 U.S.C. § 371 U.S. national stage entry of International Application PCT/US2012/031,406 having an international filing date of Mar. 30, 2012, which claims the benefit of priority to U.S. Provisional Patent Application Nos. 61/469,421, filed on Mar. 30, 2011, and 61/490,312, filed May 26, 2011, both of which are hereby incorporated by reference for all purposes as if fully set forth herein.

STATEMENT OF GOVERNMENTAL INTEREST

This invention was made with government support under grant numbers AG021334 and AG043284 awarded by the National Institutes of Health. The government has certain rights in the invention.

BACKGROUND OF THE INVENTION

The Renin Angiotensin System (RAS) is a key regulator of cardiovascular and renal function. Although many studies have focused on the impact of extracellular angiotensin II and its receptors Angiotensin II type 1 ($AT_1R$) and Angiotensin II typo 2 ($AT_2R$) on the cardiovascular system, others have reported that angiotensin II is also present in the intracellular compartment and can be released upon cell stretch to mediate cellular growth and/or apoptosis. While many of the autocrine effects of this endogenous angiotensin store are believed to be mediated by plasma membrane angiotensin receptors, an intracellular RAS acting on nuclear angiotensin receptors has also been proposed.

The RAS influences cardiovascular function via nitric oxide regulation. $AT_1R$ blockade increases nitric oxide (NO) and this increase is abolished by concomitant $AT_2R$ blockade, suggesting that the $AT_2R$ is important in NO production. $AT_2R$ likely increases NO production via direct stimulation of Nitric Oxide Synthase (NOS) or indirectly through bradykinin-dependent mechanisms.

Possible sources of NO coupled to angiotensin signalling include the three canonical NOS isoforms; neuronal (nNOS), inducible (iNOS), and endothelial NOS (eNOS). Additionally, there have been reports of a NOS isoform in mitochondria (mtNOS). Though the unique identity of mtNOS is still controversial, this mitochondria-specific isoform has been localized to the inner mitochondrial membrane, where it may regulate mitochondrial respiration. While several studies have provided evidence that angiotensin receptors can couple to the canonical NOS isoforms, nothing is known about whether intracellular angiotensin II influences mitochondrial NO production or if it has any other effects on mitochondrial function.

Mitochondria are the main site of superoxide generation that contributes to the majority of reactive oxygen species (ROS) to the cell, although other sites of ROS production within the cell are documented. The potential for ROS to induce oxidative damage has significant implications for the cellular integrity of highly metabolic, long-lived and post-mitotic tissues such as brain, heart, skin and skeletal muscle. ROS-induced accumulations in faulty proteins, oxidized fatty acids, and mtDNA mutations would result in a progressive, feed-forward, and irreversible cycle of cellular dysfunction that leads to the onset of phenotypes associated with aging. The role of mitochondria in promoting sarcopenia was uncovered by studies showing that muscle fibers containing dysfunctional mitochondria were atrophied compared to fibers that did not. Along with their role in ROS production, mitochondria play a critical role in maintaining cellular integrity through the regulation of programmed cell death, or apoptosis. Thus, the intimate connection between mitochondrial function and the viability of skeletal muscle suggests that this organelle plays a significant role in the progression of cellular aging.

Human and rodents' skin express a fully functional angiotensin system that is independently regulated and compartmentalized from the plasma circulation. The skin angiotensin system maintains a tight balance between $AT_1R$ and $AT_2R$, which change with aging and in response to insults. While during fetal life $AT_2R$ is predominantly expressed in skin (97%), the balance shifts toward AT1R with progression toward adult age. Angiotensin II levels increase in wounded skin significantly within 6 hours, and the highest levels are observed at 24 hours after wounding It has been also demonstrated that in the first three days after wounding, the expression of angiotensin II receptors was significantly enhanced in the dermis as well as in a localized band within the superficial dermis of the skin surrounding the wound. The major proportion of this increase was duo to $AT_2R$. These results are in line with the generally accepted theories on the function of $AT_2R$ in regulation of cell growth and differentiation, increase RNA synthesis, c-fos and c-jun expression in rat aortic smooth muscle cells as well as c-fos, c-myc, Transforming Growth Factor β and Platelet Derived Growth Factor (PDGF).

There still exists, therefore, an unmet need to provide novel methods for increasing wound healing and to mitigate the effects of oxidative stress on skin and soft tissues.

SUMMARY OF THE INVENTION

In accordance with an embodiment, the present invention provides for the first time, the subcellular localization of functional angiotensin II receptors (ATRs) within the inner mitochondrial membrane. The present invention also demonstrates the effects of manipulating the mitochondrial angiotensin system on mitochondrial production of nitric oxide and mitochondrial respiration. Evidence is presented herein, of age related changes in mitochondrial angiotensin receptor expression and reversal of these changes with long term use of angiotensin receptor blockers. The presence of an active angiotensin system in human mitochondria creates a novel target for treatment aiming at preserving mitochondrial function, improvement of wound healing and improve or delay the signs of aging.

In accordance with an embodiment, the present invention provides a pharmaceutical composition comprising at least one angiotensin II type 1 receptor ($AT_1R$) antagonist, or a salt, solvate, or derivative, or isoforms thereof, and a pharmaceutically acceptable carrier suitable for use in topical administration.

In accordance with another embodiment, the present invention provides a pharmaceutical composition of comprising at least one $AT_1R$ antagonist, or a salt, solvate, or derivative, or isoforms thereof, and a pharmaceutically acceptable carrier suitable for use in topical administration, for use in preparing a medicament, preferably for use in preparing a medicament for use in treating a skin lesion or wound in a mammal comprising applying a sufficient amount of the pharmaceutical composition.

In accordance with a further embodiment, the present invention provides a pharmaceutical composition of comprising at least one $AT_1R$ antagonist, or a salt, solvate, or derivative, or isoforms thereof, and a pharmaceutically acceptable carrier suitable for use in topical administration, for use in preparing a medicament, preferably for use in a medicament for augmenting wound repair in a mammal comprising topical application to skin and soft tissue injuries or wounds, for a sufficient time and under sufficient conditions to modulate the function of at least one $AT_1R$ and/or $AT_2R$, wherein the modulation of the function of the angiotensin receptor improves wound healing in mammalian subject.

In accordance with yet another embodiment, the present invention provides a pharmaceutical composition of comprising at least one $AT_1R$ antagonist, or a salt, solvate, or derivative, or isoforms thereof, and a pharmaceutically acceptable carrier suitable for use in topical administration, for use in preparing a medicament, preferably for use in a medicament for treating an inflammatory skin condition in a mammal comprising topical application to skin for a sufficient time and under sufficient conditions to modulate the function of at least one $AT_1R$ and/or $AT_2R$, wherein the modulation of the function of the angiotensin receptor increases anti-inflammatory properties and augments repair of the skin of the mammalian subject.

In accordance with an embodiment, the present invention provides an isolated mitochondrial angiotensin type 2 receptor ($AT_2R$) protein.

In accordance with another embodiment, the present invention provides a method of identifying candidate ligands that modulate function of $AT_2R$ that are localized to mitochondria in mammalian cells comprising a) obtaining a sample containing mitochondrial $AT_2R$ in an environment sufficient to maintain physiological function of the $AT_2R$, b) measuring the function of the $AT_2R$, c) contacting the sample with a candidate ligand, d) measuring the function of the $AT_2R$ in the presence of the candidate ligand, wherein a significant difference in the function of the $AT_2R$ in the presence of the candidate ligand in comparison to function in the absence of the candidate ligand is indicative that the candidate ligand modulates function of mitochondrial $AT_2R$.

In accordance with a further embodiment, the present invention provides a method for modulating aging processes in a mammalian cell by reducing the activity of $AT_1R$ comprising contacting a mammalian cell comprising mitochondria expressing both $AT_2R$ and $AT_1R$ with a compound that increases the activity of the $AT_2R$, wherein an increase in the activity of the $AT_2R$ reduces the activity of the $AT_2R$ in the cell and modulates cellular aging processes.

In accordance with an embodiment, the present invention provides a method to reduce cellular aging in mammalian cells that express mitochondrial $AT_2R$ by modulating the activity of the $AT_2R$ comprising contacting at least one mammalian cell with a compound for a sufficient time and under sufficient conditions to modulate the function of at least one mitochondrial $AT_2R$, wherein the modulation of the function of the $AT_2R$ reduces cellular aging in mammalian cells.

In accordance with another embodiment, the present invention provides a method to reduce cellular aging in a mammalian subject that expresses mitochondrial $AT_2R$ in cells by modulating the activity of the $AT_2R$ comprising administering a compound for a sufficient time and under sufficient conditions to modulate the function of at least one mitochondrial $AT_2R$, wherein the modulation of the function of the $AT_2R$ reduces cellular aging in mammalian subject.

In accordance with a further embodiment, the present invention provides a method for modulating cellular aging processes by augmenting the activity of mitochondrial $AT_2R$ in at least one mammalian cell expressing both $AT_2R$ and $AT_1R$ comprising contacting a mammalian cell with an antagonist to $AT_1R$ wherein a decrease in the activity of the $AT_1R$ augments the activity of the mitochondrial $AT_2R$ in a mammalian cell and modulates cellular aging processes.

In accordance with an embodiment, the present invention provides a method for improving muscle cell function by augmenting the activity of mitochondrial $AT_2R$ in at least one mammalian cell expressing both $AT_2R$ and $AT_1R$ comprising contacting a mammalian cell with an antagonist to $AT_1R$ wherein a decrease in the activity of the $AT_1R$ augments the activity of the mitochondrial $AT_2R$ in a mammalian cell and improves muscle cell function.

In accordance with another embodiment, the present invention provides an isolated mitochondrial interleukin 6 (IL-6) receptor protein.

In accordance with an embodiment, the present invention provides a method to identify candidate ligands that modulate function of IL-6 receptors that are localized to mitochondria in mammalian cells comprising: a) obtaining a sample containing mitochondrial IL-6 (IL-6) receptors in an environment sufficient to maintain physiological function of the IL-6 receptors, b) measuring the function of the IL-6 receptors, c) contacting the sample with a candidate ligand, and d) measuring the function of the IL-6 receptors in the presence of the candidate ligand, wherein a significant difference in the function of the IL-6 receptors in the presence of the candidate ligand in comparison to function in the absence of the candidate ligand is indicative that the candidate ligand modulates function of mitochondrial IL-6 receptors.

BRIEF DESCRIPTION OF THE DRAWINGS

FIG. 1A shows $AT_1Rs$ on human monocyte cell membrane and in the cytoplasm (1B). FIG. 1C shows labeling in close proximity to mitochondria and rarely in the mitochondria (1D).

DETAILED DESCRIPTION OF THE INVENTION

Figure 1:
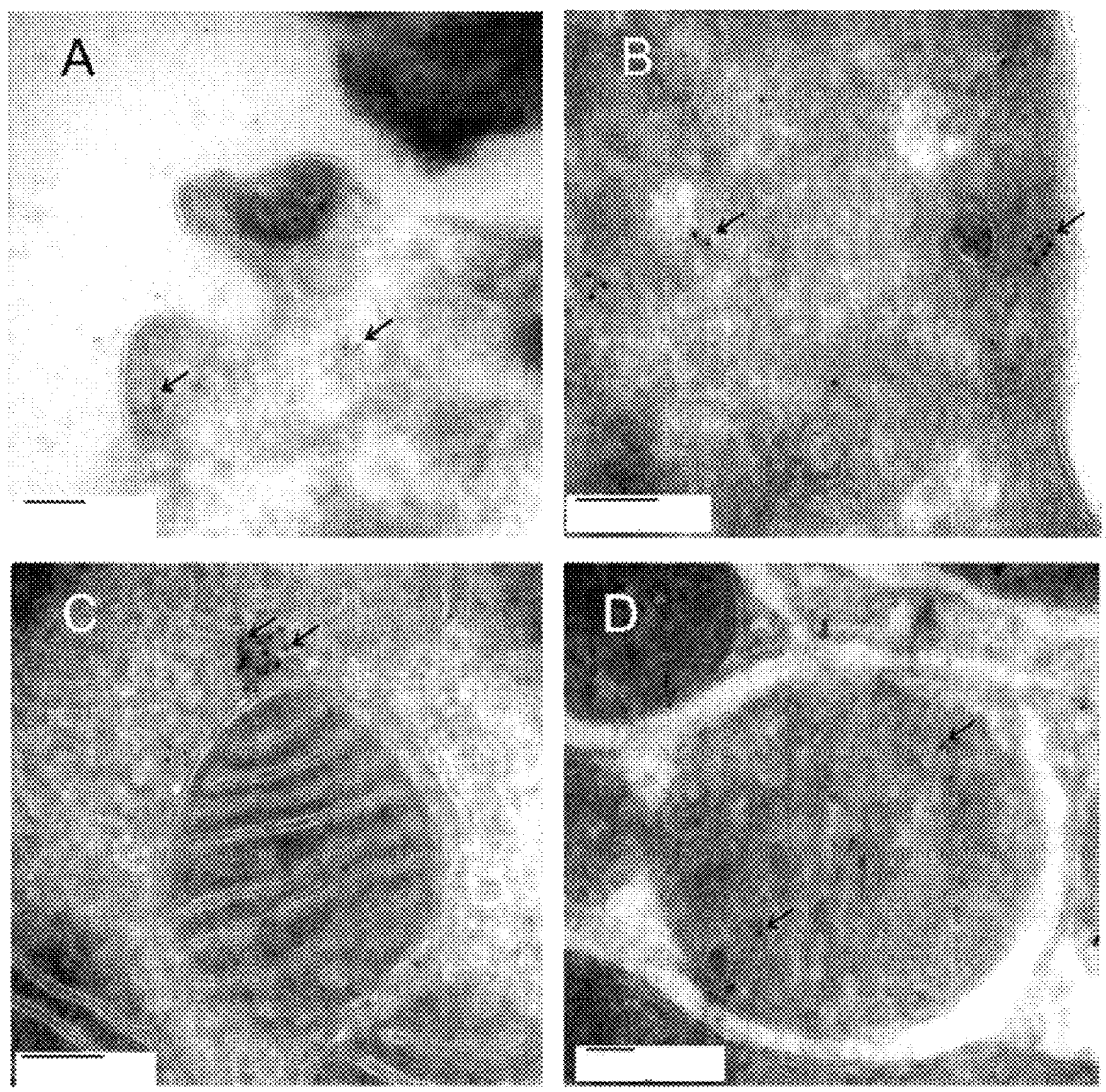
FIG. 1 is an immuno-electron microscopic localization of $AT_1Rs$ in sections of human monocyte (1A and 1B) and mouse kidney tubular cells (1C and 1D) using gold bead labeling (arrows) for $AT_1Rs$.

The present inventors are the first to document the subcellular localization of functional MAS coupled to angiotensin receptors, which opens a new area of investigation into the regulation of mitochondrial function by angiotensin II-mediated intracrine signalling. Several approaches were used to test the presence and function of a Mitochondrial Angiotensin System (MAS) provided herein, including high resolution transmission immunoelectron microscopy, confocal imaging in live cells tracking the expression of angiotensin receptors and real time measurement of mitochondrial NO production and respiration in response to activation or inhibition of the receptor(s) in isolated mitochondria.

The present inventors have reported that functional $AT_2R$ are present on the mitochondrial inner membrane and are colocalized with endogenous angiotensin II. Herein is provided that activation of the mitochondrial angiotensin system (MAS) was demonstrated to be coupled to mitochondrial nitric oxide production and can modulate respiration. The localization of $AT_2R$ in the mitochondrial inner membrane suggests its importance to nitric oxide production, which is believed to originate in the inner membrane through mtNOS. Based on the recent finding of the present inventors of a functional mitochondrial angiotensin system and recent reports on the beneficial effects of $AT_1R$ blockers on mitochondrial number and function, such a beneficial effect is now understood to be mediated via unopposed $mtAT_2R$. Selective induction of $mtAT_2R$ represents an exciting new target for therapeutic intervention for the treatment of cardiovascular, renal, neurological, and musculoskeletal disorders associated with aging and mitochondrial dysfunction.

In accordance with an embodiment, the present invention provides a pharmaceutical composition suitable for use as a topical application of angiotensin receptor blockers on skin and soft tissue. It is understood that any angiotensin receptor blocker is suitable. Examples include:

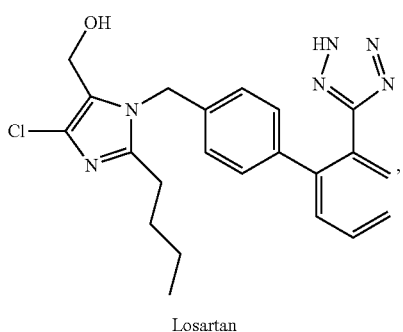

Losartan

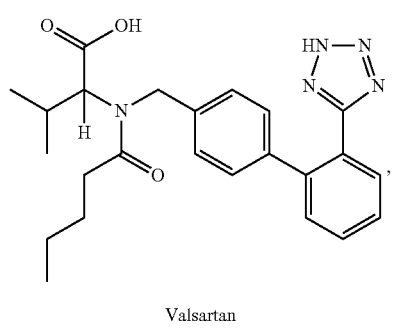

Valsartan

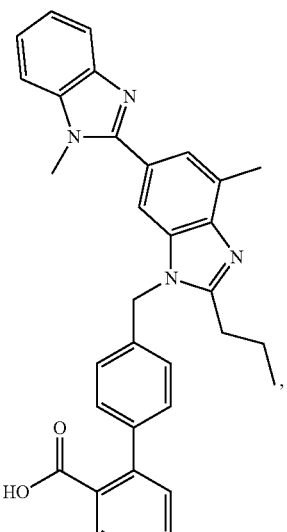

Telmisartan

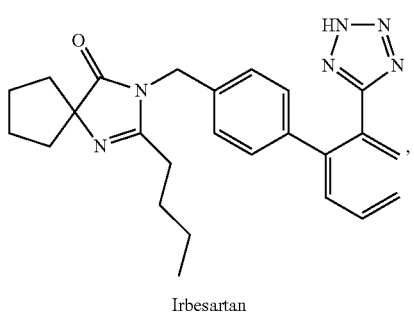

Irbesartan

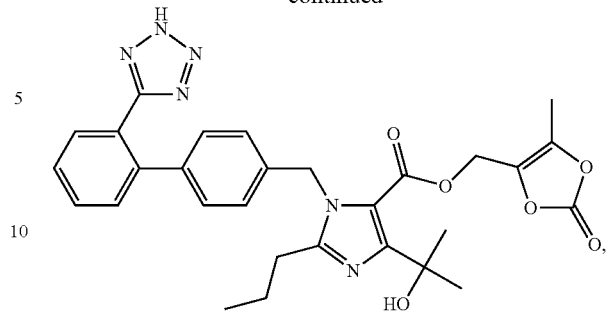

Olmesartan

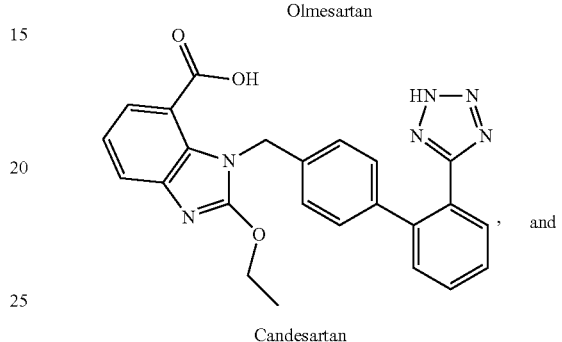

Candesartan, and

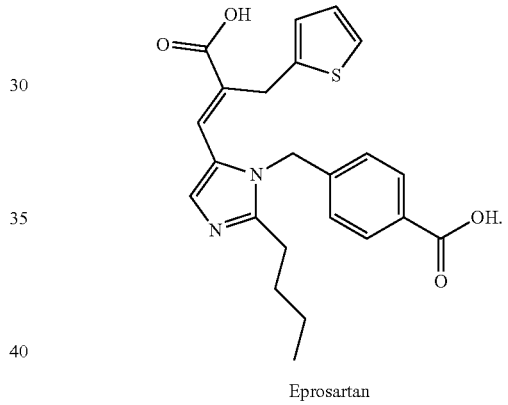

Eprosartan

One of ordinary skill in the art would appreciate that salts, solvates, analogs and derivatives of the disclosed agents and related agents also are suitable for use with the presently disclosed methods. As used herein, an "analog" refers to a chemical compound in which one or more individual atoms or functional groups of a parent compound have been replaced, either with a different atom or with a different functional group.

In accordance with an embodiment, the present invention provides a pharmaceutical composition comprising at least one $AT_1R$ antagonist, or a salt, solvate, or derivative, or isoforms thereof, and a pharmaceutically acceptable carrier suitable for use in topical administration.

It is understood by those of ordinary skill, that the composition can be applied topically at injured, inflamed, scarred or damaged skin, subcutaneous or skeletal muscle areas.

In accordance with an embodiment, the present invention can also include a second therapeutic or active agent.

In accordance with an embodiment, the pharmaceutical compositions of the present invention are suitable for use in preparing a medicament, preferably for use in preparing a medicament for use in treating a skin lesion or wound in a mammal comprising applying a sufficient amount of the pharmaceutical composition of the present invention at the site of the skin lesion or wound.

In accordance with another embodiment, the pharmaceutical compositions described herein can be used in preparing a medicament, preferably for use in a medicament for treating an inflammatory skin condition in a mammal comprising topical application to skin for a sufficient time and under sufficient conditions to modulate the function of at least one $AT_1R$ and/or $AT_2R$, wherein the modulation of the function of the angiotensin receptor increases anti-inflammatory properties and augments repair of the skin of the mammalian subject. In another embodiment, the inflammatory skin condition being treated is acne. In a further embodiment, the inflammatory skin condition is due to aging, including remitative effects such as, for example, vasodilatation, growth, differentiation, impaired inflammatory signaling cascades, production of nitric oxide, inhibition of fibroblast proliferation, and modulation of apoptosis. Other effects due to cellular aging, including the aging of skin and soft tissues, which are treated by the compositions and methods described herein are selected from the group consisting of: decrease in volume and elasticity, low cutaneous blood flow, lower glandular activity, laxity (sagging), rhytids (wrinkles), erythema/telangiectasia (redness), dyspigmentation (brown discoloration), solar elastosis (yellowing), keratoses (abnormal growths) and poor texture.

In accordance with an embodiment, the pharmaceutical compositions described herein can be used in preparing a medicament, preferably for use in a medicament for treating chronic wounds or ulcers of the skin or soft tissue. Examples of such wounds include diabetic sores and ulcers.

In accordance with an embodiment, the pharmaceutical compositions described herein can be used in preparing a medicament for use in modulating the wound healing response in the skin of a mammal, comprising topical application of the compositions in an effective amount for a sufficient period time. As used herein, the term "modulating the wound healing response" means the prevention or down-regulation of the pathological response to tissue injury, which is characterized by fibrosis, including for example, production of keloids and hypertrophic scars in the skin, tendon adhesions, transmission blockage following nerve injury, scleroderma, Crohn's disease, esophageal strictures, urethral strictures, capsules around breast implants, liver cirrhosis, atherosclerosis and fibrotic non-union in bone. Chronic non-healing dermal ulcers are also examples of the pathological response to tissue injury.

In another embodiment, the present invention provides a method for prevention or treatment of fibrosis (or hypertrophic scarring) in a wound in the skin of a mammal comprising administering topically to the wound at about 3 to about 20 days post wounding, an effective amount of the pharmaceutical compositions described herein for a sufficient time to prevent fibrosis or hypertrophic scarring.

It will be understood by those of ordinary skill in the art that surprisingly, the wound healing by the compositions and methods of the present invention is improved when administered to the subject a number of days after the wound is received. In accordance with an embodiment, the topical application of the compositions of the present invention to the wound should begin about 3 to about 20 days post wounding, preferably about 5 to about 10 days post wounding, and more preferably about 7 days post wounding.

In accordance with an embodiment, it is understood that the cells that express mitochondrial $AT_2R$ are selected from the group consisting of skin or any soft tissue.

In accordance with an embodiment, the present invention provides a method of identifying candidate ligands that modulate function of $AT_2R$ that are localized to mitochondria in mammalian cells comprising: a) obtaining a sample containing mitochondrial angiotensin type 2 receptors ($AT_2R$) in an environment sufficient to maintain physiological function of the $AT_2R$, b) measuring the function of the $AT_2R$, c) contacting the sample with a candidate ligand, d) measuring the function of the $AT_2R$ in the presence of the candidate ligand, wherein a significant difference in the function of the $AT_2R$ in the presence of the candidate ligand in comparison to function in the absence of the candidate ligand is indicative that the candidate ligand modulates function of mitochondrial $AT_2R$.

In some embodiments of the present invention, the candidate ligand is an agonist of mitochondrial $AT_2R$. In other embodiments of the present invention, the candidate ligand is an antagonist of mitochondrial $AT_2R$.

In other embodiments of the present invention, the candidate ligand is selected from the group consisting of the $AT_2R$ agonist CGP42112A and the $AT_2R$ antagonist PD123319.

In accordance with another embodiment, the present invention provides a method of identifying candidate ligands, wherein the function of mitochondrial $AT_2R$ is selected from the group consisting of reduction of oxidative damage, preservation of mitochondrial function, maintaining muscle cell function, and upregulation of expression.

In accordance with still another embodiment, the present invention provides a method to reduce cellular aging in a mammalian subject that expresses mitochondrial $AT_2R$ in cells by modulating the activity of the $AT_2R$ comprising administering a compound for a sufficient time and under sufficient conditions to modulate the function of at least one mitochondrial $AT_2R$, wherein the modulation of the function of the $AT_2R$ reduces cellular aging in mammalian cells or in a mammalian subject.

In some embodiments of the present invention, the alteration of cellular aging is selected from the group consisting of: vasodilatation, growth, differentiation, reduced inflammatory signaling cascades, production of nitric oxide, inhibition of fibroblast proliferation, and modulation of apoptosis.

In other embodiments of the present invention, the alteration of cellular aging is selected from the group consisting of: vasoconstriction, reduction of growth, proliferation, increased inflammatory signaling cascades, production of $O_2^-$, stimulation of fibroblast proliferation, and modulation of apoptosis.

In some embodiments of the present invention, the cells that express mitochondrial $AT_2R$ are selected from the group consisting of skeletal muscle cells, monocytes, kidney cells and heart cells.

In accordance with another embodiment, the present invention provides a method for modulating cellular aging processes by augmenting the activity of mitochondrial $AT_2R$ in at least one mammalian cell expressing both $AT_2R$ and $AT_1R$ comprising contacting a mammalian cell with an antagonist to $AT_1R$ wherein an decrease in the activity of the $AT_1R$ augments the activity of the mitochondrial $AT_2R$ in a mammalian cell and modulates cellular aging processes and/or improves muscle cell function.

In some embodiments of the present invention, the $AT_1R$ antagonist is an angiotensin type receptor blocker.

In other embodiments of the present invention, the angiotensin type receptor blocker is selected from the group consisting of losartan and valsartan, telmisartan, irbesartan, olmesartan, candesartan, and eprosartan.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject.

Non-limiting examples of biologically active agents suitable for use in the compositions of the present invention include for example, adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

Specific examples of useful biologically active agents the above categories include: analgesics, such as nonsteroidal anti-inflammatory drugs, salicylates; antihistamines, such as $H_1$-blockers and $H_2$-blockers; anti-infective agents, such as antihelmintics, antianaerobics, antibiotics, aminoglycoside antibiotics, antifungal antibiotics, cephalosporin antibiotics, macrolide antibiotics, miscellaneous antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, and scabicides.

Accordingly, included within the compositions of the present invention are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compositions of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

As used herein, the term "treat," as well as words stemming therefrom, includes preventative as well as disorder remitative treatment. The terms "reduce," "suppress," "prevent," and "inhibit," as well as words stemming therefrom, have their commonly understood meaning of lessening or decreasing. These words do not necessarily imply 100% or complete treatment, reduction, suppression, or inhibition.

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

In addition, in an embodiment, the compositions of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), antioxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compositions, as well as by the particular method used to administer the compound. Accordingly, there are a variety of suitable formulations of the pharmaceutical compositions of the invention.

For purposes of the invention, the amount or dose of the compositions, salts, solvates, or steretoisomers of any one the angiotensin receptor blockers, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compositions, salts, solvates, or stereoisomers of any one the angiotensin receptor blockers, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 1000 mg/kg body weight of the subject being treated/day, from about 0.01 to about 100 mg/kg body weight/day, about 0.1 mg to about 10 mg/kg body weight/day.

In one embodiment, the compositions of the present invention provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all or substantially the entire compound is released immediately after administration.

In yet another embodiment, the compounds of the present invention can be delivered in a controlled release system. For example, the agent may be administered using intravenous infusion, an implantable osmotic pump, a transdermal patch, or other modes of administration. In an embodiment, a pump may be used. In one embodiment, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

The pharmaceutical compositions of the present invention may also include incorporation of the active ingredients into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In accordance with the present invention, the compositions of the present invention may be modified by, for example, the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compositions are known to exhibit substantially longer half-lives in blood following intravenous injection, than do the corresponding unmodified compounds. Such modifications may also increase the compounds' solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently, or in lower doses than with the unmodified compound.

As used herein, a "derivative" refers to a chemical compound which is derived from or obtained from a parent compound and contains essential elements of the parent compound but typically has one or more different functional groups. Such functional groups can be added to a parent compound, for example, to improve the molecule's solubility, absorption, biological half life, and the like, or to decrease the toxicity of the molecule, eliminate or attenuate any undesirable side effect of the molecule, and the like. An example of a derivative is an ester or amide of a parent compound having a carboxylic acid functional group.

A derivative, as used herein, can also mean a metabolite of the angiotensin receptor blockers used in the compositions of the present invention. Examples of metabolites, include E-3174, valeryl 4-hydroxy valsartan, EXP3179, CV-11974 and enoltasosartan.

In a further embodiment, the present invention provides a method decreasing the visible signs of aging in the skin of a subject, the method comprising: administering to the subject a pharmaceutically acceptable composition comprising the $AT_1R$ antagonist is an angiotensin type receptor blocker in a therapeutically effective amount such that the cellular aging processes in the skin of the subject are decreased to an amount sufficient to decrease visually discernable aging in the skin of the subject.

An "effective amount" of an agent refers to the amount of the agent sufficient to elicit a desired biological response. As will be appreciated by one of ordinary skill in the art, the absolute amount of a particular agent that is effective can vary depending on such factors as the desired biological endpoint, the agent to be delivered, the target cell or tissue, and the like. One of ordinary skill in the art will further understand that an effective amount can be administered in a single dose, or can be achieved by administration of multiple doses.

The compositions can be administered to a subject via any suitable route or routes. In a preferred embodiment of the invention, the agent is administered topically, prepared by art recognized procedures. Dosage schedules of the drugs according to the methods of the invention will vary according to the particular compound or compositions selected, the route of administration, the nature of the condition being treated, the age and condition of the patient, the course or stage of treatment, and will ultimately be at the discretion of the attending physician.

The compositions may be specifically formulated for administration by any suitable route as described herein and known in the art. Compositions for topical delivery include, but are not limited to colloids, patches and microemulsions. Other suitable administration forms for the above and other include sprays, ointments, cremes, gels, pastes, dermal patches, etc.

In some embodiments, the pharmaceutical formulations of the invention also include a physiologically acceptable diluent or vehicle. The selection of a suitable diluent will depend upon the type of pharmaceutical formulation (e.g., solution, dispersion, emulsion, etc.), and is readily determined by those skilled in the art of pharmaceutical sciences.

In some embodiments, the formulation can include, in addition to the agent, excipient, diluent, additives, suspending agents and thickening agents, and liposomes or other microparticulate systems. In one embodiment, the agent is suspended in glycerol and vanicream. Suspensions may be prepared using techniques known the in art of pharmaceutical sciences In some embodiments, the pharmaceutical compositions are administered in a topical formulation in an amount in the range of at least about 1%-10% of therapeutic agent, in the range of at least about 11-20%, in the range of at least about 21-30%, in the range of at least about 31%-40%, in the range of at least about 41%-50%, in the range of at least about 51%-60%, in the range of at least about 61%-70%, in the range of at least about 71%-80%, in the range of at least about 81-90%, or in the range of at least about 91%-100%.

In an embodiment of the invention, the angiotensin receptor blockers can include but are not limited to the above mentioned angiotensin receptor blockers is dispersed in glycerol and then incorporates into the Vanicream. After the powder is dispersed, it is mixed with the cream. The tablets are then crushed using mortar and pestle, and dispersed in a small volume of glycerol and incorporated into the Vanicream. A small volume of glycerol (ex. 5 mL or 10 mL based on how many tablets are crushed) is measured out and added to the powder. After the powder is dispersed, it is mixed with the cream. Some of the glycerol is left to wash out the mortar of the left over losartan powder and to also mix with the cream.

In one embodiment of the invention, the therapeutic agent is prepared as follows. the strength of the cream is calculated by obtaining the weight of the angiotensin receptor blocker, the weight the amount of cream needed, and the weight of glycerol is calculated (multiply volume by the density 1.261 g/mL), then add all the weights are added. In order to produce a 10% Losartan Cream: 2 g of Losartan, 20 g of Vanicream and, and 7 ml of glycerol were used.

EXAMPLES (0094) Isolation of Mitochondria. For functional assays, crude mitochondria from animal groups were separated using differential centrifugation (Methods. 2002 April; 26(4):298-306).

Electron microscopy imaging of isolated mitochondria showed minimal contamination of the isolated mitochondria with other cell fractions.

For functional assays, crude mitochondria from animal groups were separated by using differential centrifugation as described above. Electron microscopy imaging and Western blot analysis of isolated mitochondria showed minimal contamination of the isolated mitochondria with other cell fractions. For structural and morphological studies, mouse liver, heart, kidney, and brain cells were subjected to fractionation into whole cell homogenate, post nuclear, crude mitochondria, density-purified mitochondria, mitoplast, and inner mitochondrial membrane fractions. Density-purified mitochondria were isolated on a discontinuous Percoll/HistoDenz gradient. Mitochondrial subfractions were prepared by sucrose density-gradient centrifugation essentially as described for pig heart mitochondria with minor variations. Briefly, gradient-pure mitochondria were subjected to hypotonic swelling in ~1.5 L of 20 mM $KH_2PO_4$ for 40 minutes, at which point they were centrifuged at 8,000×g to pellet swollen mitoplasts. The swollen mitoplasts were resuspended in 250 mM sucrose homogenized with a dounce homogenizer to dislodge the outer mitochondrial membrane. The solution was layered onto a discontinuous sucrose gradient consisting of 25.2%, 37.7%, 51.7%, and 61.5% layers. Sucrose gradients were centrifuged at 77,000×g for 90 minutes at 4° C. Light membranes containing outer membrane markers were collected from the 37.7%/51.7% sucrose interface. This fraction is known hereafter as the outer mitochondrial membrane-enriched fraction. Mitoplasts were collected, diluted in 250 mM sucrose, and homogenized in a dounce homogenizer. The suspension was centrifuged at 100,000×g for 30 minutes to pellet membranes. The supernatant (containing matrix proteins) was decanted. The pellet was resuspended in 10 mM Tris (pH 8.0)/250 mM sucrose, sonicated at 20 W for 1 minute on ice, and then layered onto a second sucrose density gradient. The outer and inner mitochondrial membrane fractions were stored as frozen pellets at −80° C. until required.

Western Blot Analysis. Typically, 10 µg of protein from either tissue homogenates or mitochondrial preparations were isolated from mouse kidney, heart, skin or brain and resolved by 12% SDS/PAGE. Proteins were and transferred to nitrocellulose membranes by using the iBlot transfer apparatus (Invitrogen) for 7.5 minutes. Membranes were blocked with 5% skim milk in TBS at room temperature for 1 hour. Each membrane was then incubated with one of the following primary antibodies at room temperature for 1 hour to detect cell membrane, mitochondrial, outer mitochondrial membrane, and inner mitochondrial membrane markers, respectively: mouse monoclonal anti-Na+/K+ ATPase at a dilution of 1:500 in 2% skim milk/TBS with 0.1% (vol/vol) Tween-20 (TBS-T) (c4646; Santa Cruz Biotechnology); mouse monoclonal anti-cytochrome c oxidase (CoxIV) at a dilution of 1:500 in 2% skim milk/TBS-T (A-6403; Molecular Probes); mouse monoclonal anti-voltage-dependent anion channel (VDAC) at a dilution of 1:500 in 2% skim milk/TBS-T (A-31855; Invitrogen); and mouse monoclonal anti-ATP synthase β at a dilution of 1:2,500 in 2% skim milk/TBS-T (A-21350; Invitrogen). In addition, membranes were incubated with a rigorously validated, well-characterized anti-angiotensin (Ang) type 2 receptor ($AT_2R$) antibody (sc-9040; Santa Cruz Biotechnology), anti-Ang (Santa Cruz Biotechnology), and anti-Ang type 1 receptor ($AT_1R$) antibody (Santa Cruz Biotechnology).

To confirm the absence of cross-reactivity of these antibodies, we studied Chinese hamster ovary (CHO) cells lacking $AT_1R$ and $AT_2R$. Using immunoblot detection, we were able to detect $AT_1R$ and $AT_2R$ in positive controls but not in the CHO cells. After washing with PBS, the membranes were further incubated with respective secondary antibodies conjugated with horseradish peroxidase (Dako) 1:1,000 in 2% skim milk/TBS-T at room temperature for 1 hour. Immunoreactive protein bands were visualized on film (Kodak X-Omat AR5) with SuperSignal West Pico chemiluminescence substrate (Pierce Biotechnology).

Transfection of Human Fibroblast Cells. Human fibroblast cells maintained in antibiotic-free DMEM supplemented with 10% FBS (BioMedia) and 2 mM L-glutamine (Invitrogen) were seeded in 35-mm glass-bottom dishes. Human $AT_2R$ cDNA was purchased from Invitrogen as a recombination ultimate human ORF. To construct a mammalian expression vector, the $AT_2R$ cDNA was cloned into the destination vector, pcDNA-Dest53, to create a pcDNA-GFP $AT_2R$. As a positive control, pcDNA-EGFP-Cl was used. As a negative control, pcDNA-Dest47 with a termination sequence was used. When $AT_2R$ is expressed in the pcDNA-Dest47, the polymerase reads ATG2 sequence but, instead of making a fusion protein with Cycle 3 GFP, the ATG2 sequence is terminated, resulting in bicistronic construct expression of ATG2 and GFP. Human fibroblast cells were transiently transfected with 1 µg of DNA of pcDNA-Cycle 3 GFP-$AT_2R$, positive control pcDNAEGFP, or negative control pcDNA $AT_2R$-Cycle 3 GFP by using Lipofectamine transfection reagent. The expression of recombinant $AT_2R$ with an N-terminal cycle 3 GFP was confirmed by RT-PCR and DNA sequencing. Images of transfected human fibroblast cells were acquired with the Zeiss Meta Confocal Laser Scanning Microscope System using AIM software. An Ar laser exciting at 488 nm and a red He/Ne laser at 543-nm wavelengths were used to obtain optical sections. Narrow-band emission filters (nm) were used to eliminate channel cross-talk, and a 1.0-µm confocal aperture was used to obtain Z-plane sections. Slides were imaged with a 100× oil-immersion plan apo objective lens (n.a., 1.4) through a Zeiss Axiovert inverted microscope.

Measurement of Nitric Oxide (NO) Production in Isolated Mitochondria. Kidney mitochondria were isolated by homogenization and differential centrifugation in a medium containing 3.4 nmL of 1 M sucrose, 12 mL of 1 M mannitol, 2.5 mL of 1 M KCL, 1 M Tris-HCL, 0.5 mL of 1 M EDTA, 1.5 mL of 0.1 M EGTA, and 0.1% BSA (pH 7.4). Mitochondria were suspended in incubation solution. Total mitochondrial protein was determined by a Lowry Protein Assay Kit (Sigma-Aldrich). To directly monitor real-time changes in NO production from isolated mitochondria in response to specific AT2R agonists (CGP421140 at 10 nM and 100 nM) and antagonists (PD-123319 at 100 nM and 1 µM), the NO fluorescent molecular detection probe kit (Enzo Life Sciences) was used according to the manufacturer's instructions. Briefly, isolated mitochondria were incubated under normal tissue-culture conditions with nonfluorescent, cell-permeable NO detection dye that reacts with NO in the presence of $O_2$ with high specificity, sensitivity, and accuracy, yielding a water-insoluble red fluorescent product. Isolated mitochondria were then treated for 30 minutes with the NO scavenger 2-(4-carboxyphenyl)-4,4,5,5-tetramethyl-imidazoline-1-oxyl-3-oxide (c-PTIO) followed by a 15-minute incubation with AT2R agonists and/or antagonists. Separate positive control samples were treated with the NO inducer L-arginine, and neg-ative control samples were generated by treatment with NO scavenger (c-PTIO). The fluorescent products were measured by using a reader equipped with Cyanine 5 (650/670 nm).

Immunolocalization of $AT_1R$, $AT_2R$, and Ang. Immunogold electron microscopy was performed as described (Am. J. Physiol. Endocrinot. Metab., 286:E1011-E1022 (2004)). In brief, mouse tissues were fixed in 4% formaldehyde in 0.1 M sodium cacodylate supplemented with 3% sucrose (wt/vol) and 3 mM CaCl2 and cryoprotected in 2.3 M sucrose overnight in polyvinylpyrrolidone (Sigma). Ultrathin sections were cut on a Leica Ultracut UCT microtome, and sections were placed on Formvar-coated nickel 200-mesh hexagonal grids. The sections were incubated in primary antibody against rabbit anti-AT2R, goat anti-Ang, or goat anti-AT1R antibody overnight at 4° C. at a concentration of 10 µg/mL. We used a rigorously validated, well-characterized anti-AT2R antibody (J. Am. Soc. Nephrol. 13:1162-1171 (2002); Hypertension 40:335-341 (2002); Proc. Natl. Acad. Sci. USA 100:7454-7459 (2003) (Santa Cruz Biotechnology), anti-Ang antibody (J. Clin. Invest. 117:1088-1095 (2007); Brain Res 1008:224-235 (2004); Brain Res 1008:212-223 (2004) (Santa Cruz Biotechnology), and anti-$AT_1R$ antibody (Cell. Biochem. Funct. 28:58-65 (2010)) (Santa Cruz Biotechnology). To confirm the absence of cross-reactivity of these antibodies, we studied CHO cells lacking $AT_2R$. Using a Pierce immunoaffinity matrix with subsequent immunoblot detection, we were able to detect $AT_2R$ in positive controls but not in the CHO cells. Primary antibodies were detected with either 6-nm colloidal gold donkey anti-goat or 12-nm colloidal goat anti-rabbit (Jackson ImmunoResearch) diluted 1:20 in PBS for 1 hour. Final contrasting of the sections was done by incubating them in 2% methyl cellulose (Sigma) and 0.3% uranyl acetate (Ted Pella) for 10 min at 4° C. All sections were viewed with a Philips CM 120 TEM transmission electron microscope at an accelerating voltage of 80 kV. Images were taken with a Gatan Orius SC 1000 digital camera. Photographs for representative sections were taken.

Mitochondrial Respiration. For monitoring respiration, isolated mitochondria from rat heart or liver (10 µg of protein per well) were aliquoted into 96 wells of a polyethyleneimine-coated XF96 cell culture microplate (Seahorse Bioscience). The plate was centrifuged at 3,000×g for 10 minutes at 4° C. in an A-4-62 rotor, which control experiments determined caused an attachment of isolated mitochondria that was sufficiently robust to withstand the mixing protocols of the machine. Mitochondria were placed in 300 µL per well of mitochondrial buffer [20 mM Hepes, 137 mM KCl, 2.5 mM MgCl2, 2 mM K2HPO4, 0.5 mM EGTA, and 0.2% (wt/vol) BSA (pH 7.3) at 37° C.]J. Plates were used immediately. The cell culture microplate was incubated and loaded into the Seahorse XF96 extracellular flux analyzer following the manufacturer's instructions. All experiments were performed at 37° C.

Oxygen consumption rate data points refer to the mean rates during the measurement cycles, which consisted of a mixing time of 30 s and a wait time of 2 minutes followed by a data acquisition period of 10 minutes (50 data points). Mitochondrial substrates glutamate/malate (Sigma-Aldrich) or succinate (Sigma-Aldrich) were added to a final concentration of 5 mM. ADP (Sigma-Aldrich) was added to a final concentration of 1 mM. AT2R agonist CGP421140 (Sigma-Aldrich) was added to a final concentration of 0.1 nM to 10 µM. AT2R antagonist PD-123319 (Sigma-Aldrich) was added at a final concentration of 1 µM. An arginine analog that inhibits NO production, L-NG-nitroarginine methyl ester (L-NAME; Sigma-Aldrich), was added at a final concentration of 1 µM. The oxygen consumption rates were determined by using a compartment model-based deconvolution algorithm, which compensated for oxygen diffusion phenomena occurring around the entrapped volume and for the response time of the probe.

Mitochondrial Membrane Potential and NADH Measurements. Inner membrane potential of isolated mitochondria ($\Delta\psi$m) was quantified ratiometrically in a wavelength-scanning fluorometer (QuantaMaster; Photon Technologies International) with tetramethylrhodamine methyl ester (TMRM) fluorescence, as described previously (Biophys J. 76:469-477 (1999)). Isolated mitochondria were equilibrated with 50 nmol/L TMRM in the incubation medium for 5 minutes. Changes in $\Delta\psi$m with increasing concentrations of the AT2R agonist CGP421140 were quantified from the TMRM fluorescence ratio (573/546 nm excitation ratio with 590 nm emission), with calibration constants previously determined for isolated mitochondria incubated under identical conditions. NADH fluorescence was measured simultaneously with 350-nm excitation and 450-nm emission wavelengths.

Human and Animal Groups. Mitochondria were studied in adult human monocytes (20-30 y old), adult human skeletal muscle tissue, adult rats (24 wk old), adult (20 wk old) and aged (70 wk old) mice, and a human cell line. Adult mice at 50 wk of age were treated with the AT1R blocker losartan at doses of 40-60 mg/kg per day for 20 wk. All experiments were approved by the Johns Hopkins Animal Care and use Committee and the Johns Hopkins Institutional Review Board. Weight, blood urea nitrogen, creatinine, and albumin were measured in adult (20 wk) and aged (70 wk) mice and in aged mice on losartan treatment. There was no significant difference in any of the above measured indices during the time of treatment (data not shown). As to additional characterization of animals used in this study, the dose of losartan used in this study led to a 10-15% decrease in blood pressure. We visually inspected each animal carcass after the dissection for any abnormalities. In our small sample (10 animals per group), we did not observe any evidence of malignancy. In addition, all of the animals in the control and treatment groups showed no evidence of decreased activity or illness.

Statistical Analyses. Each experiment was performed at least two times. Triplicate cultures were included in each treatment group. Data are expressed as means±SD and analyzed with the oneway ANOVA program. Differences were considered significant at P<0.05, as determined by the Student-Newman-Keuls method for pairwise multiple comparisons.

Example 1

Figure 2:
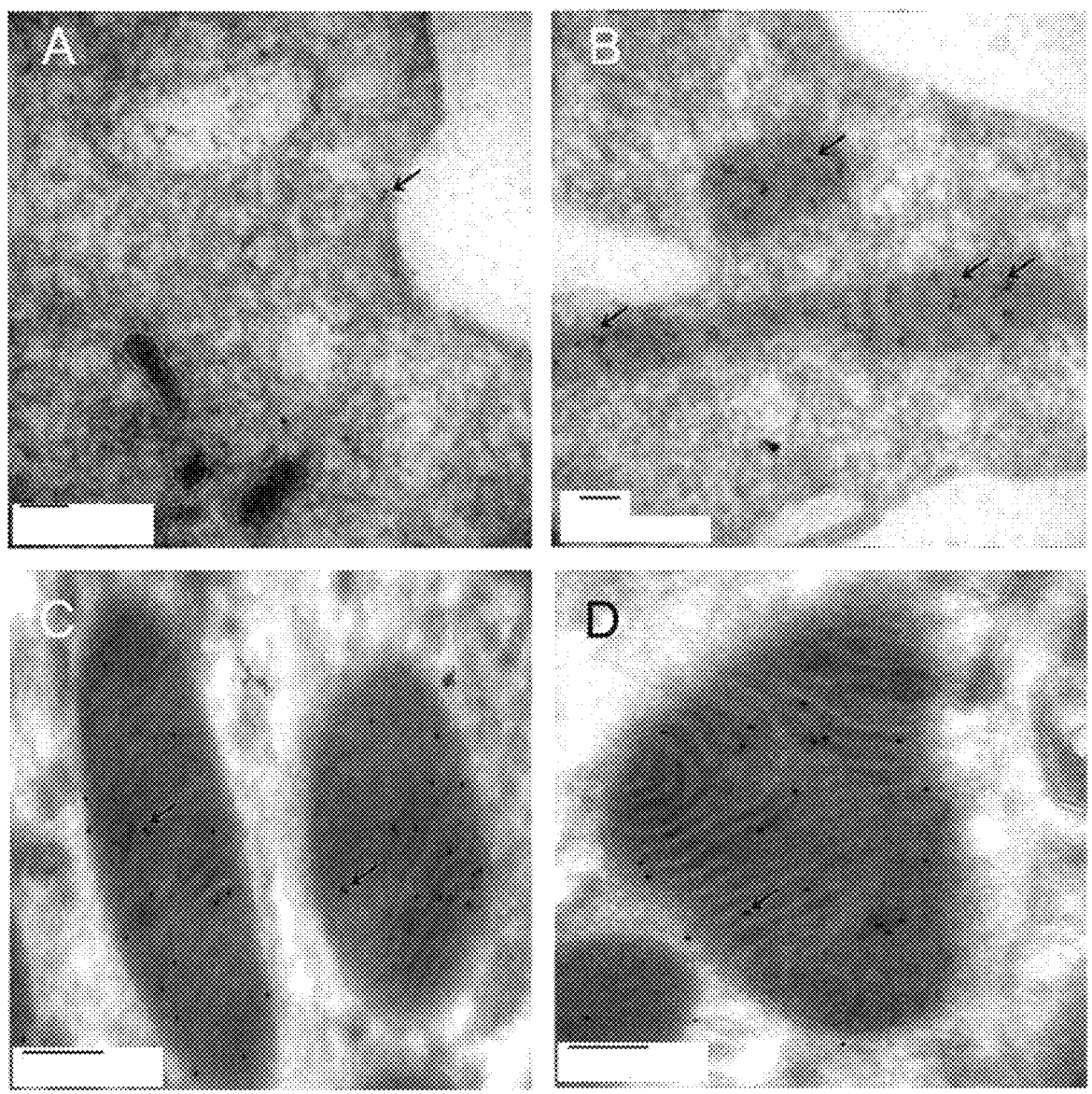
FIG. 2 is an immuno-electron microscopic localization of $AT_2Rs$ in sections of human monocyte (2A and 2B) and mouse renal tubular cells (2C and 2D) using gold beads labeling (arrows) for $AT_2Rs$. 2A shows $AT_2Rs$ on human monocyte cell membrane, and 2B-2D reveal heavy labeling for $AT_2Rs$ within mitochondria.

Subcellular Distribution of $AT_1Rs$ and $AT_2Rs$. The subcellular distribution of $AT_1Rs$ and $AT_2Rs$ was assessed by high resolution immunoelectron microscopy in human monocytes, skeletal myocytes and in cardiac myocytes, renal tubular cells, neuronal cells, vascular endothelial cells, and hepatocytes from CS7BL/6 mouse, using specific polyclonal antipeptide antibodies. $AT_1R$ immunoreactivity was observed in the cell membrane of human monocytes (FIG. 1A). $AT_1R$ did not appear in the mitochondria from young adult monocytes or animal tubular kidney cells (FIGS. 1B and 1C) except in rare occurrences (FIG. 1D), but was consistently found not far from the mitochondrial outer membrane (FIG. 1C). $AT_2R$ immunoreactivity was observed in the cell membrane of human monocytes (FIG. 2A). Abundant mitochondrial $AT_2R$ (mt$AT_2R$) was also observed in human monocytes and mouse tissues (FIG. 2B-D). To confirm the immunoelectron microscopy findings, mouse heart homogenates were fractionated first by differential centrifugation and subsequently by density gradient centrifugation. The density-purified mitochondria were probed with specific antibodies. $AT_2R$ immunoreactivity increased with progressive purification of mitochondria, for which cytochrome c oxidase (Cox IV) was used as a marker. Importantly, the immunorcactivity of Na+/K+ ATPase, a plasma membrane marker, declined with progressive enrichment of mitochondria. This is consistent with mitochondrial enrichment of $AT_2Rs$ (data not shown). In contrast, $AT_1Rs$ did not enrich with mitochondrial fractions. The relative expression of $AT_2Rs$ per mitochondria in cells obtained from different human and mouse tissues was quantified through EM.

Example 2

Figure 3:
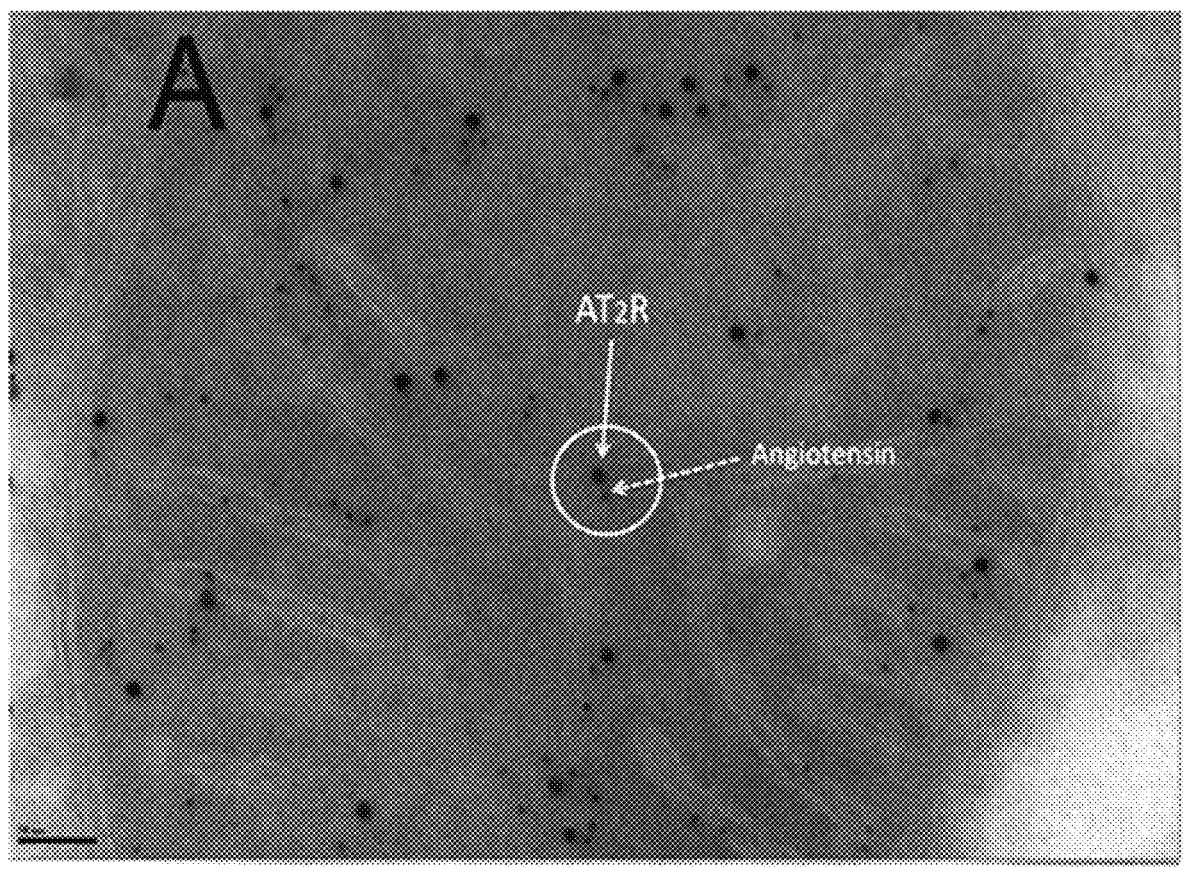
FIG. 3 shows immunoelectron microscopic localization of $AT_2R$ binding to Ang in the mitochondria by using a gold-labeled anti-$AT_2R$ antibody (12 nm gold) and a gold-labeled anti-Ang antibody (6 nm gold). Shown is colocalization of $AT_2Rs$ with Ang in sections of mouse hepatocytes (3A), kidney tubular cells (3B) neurons (3C), and cardiac myocytes (3D).
Figure 3:
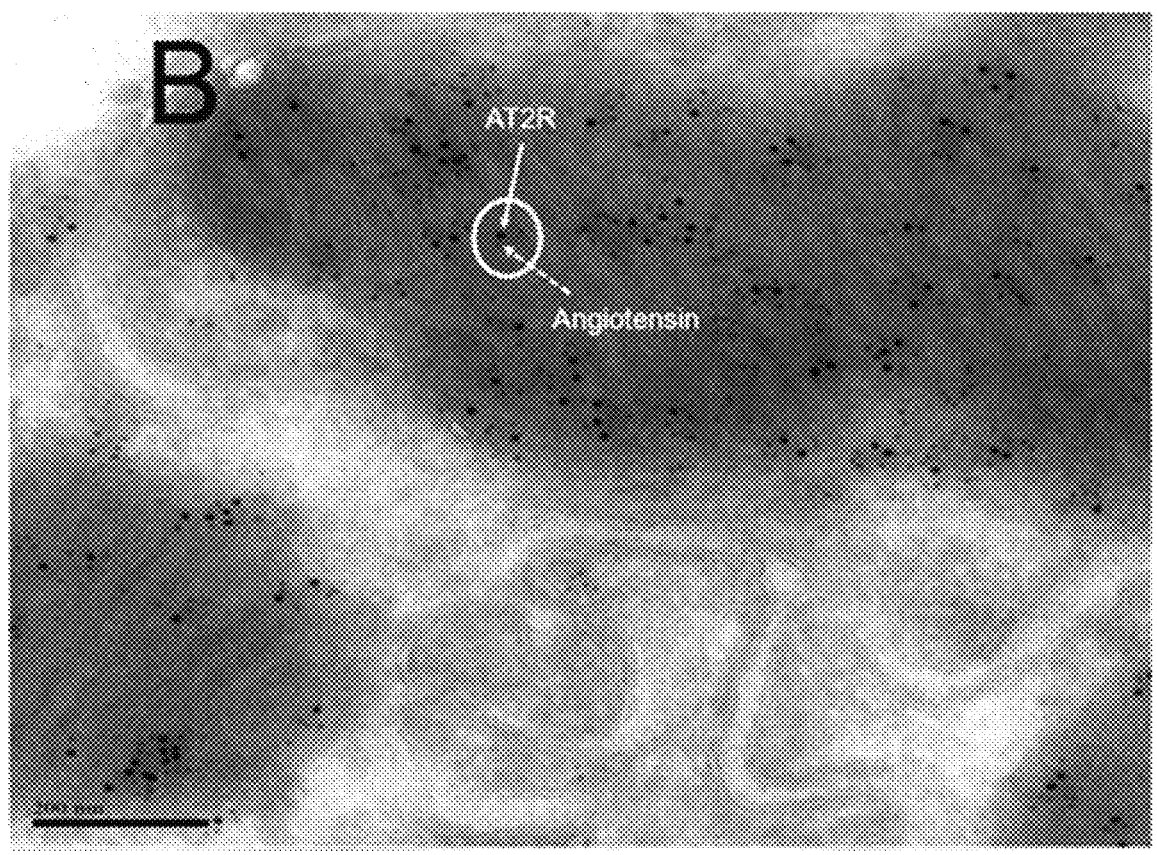
Figure 3:
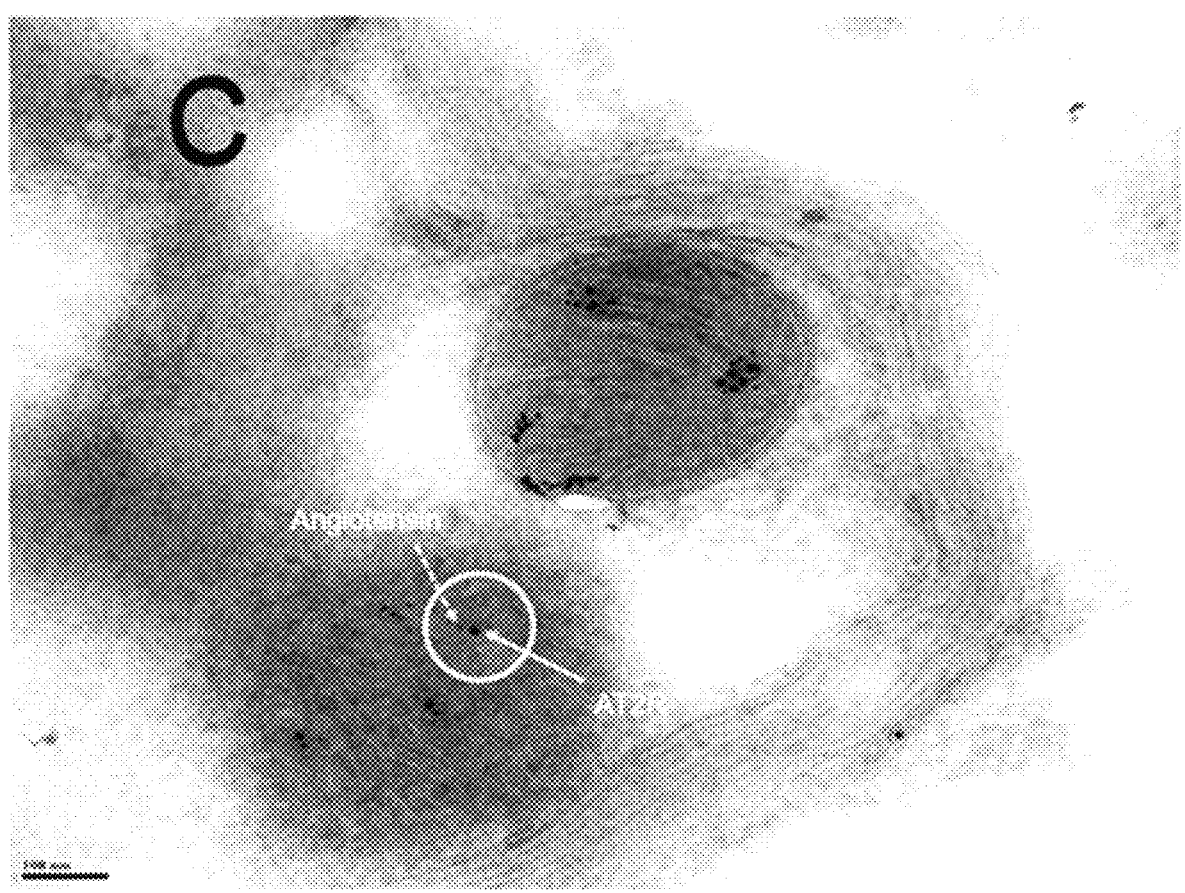
Figure 3:
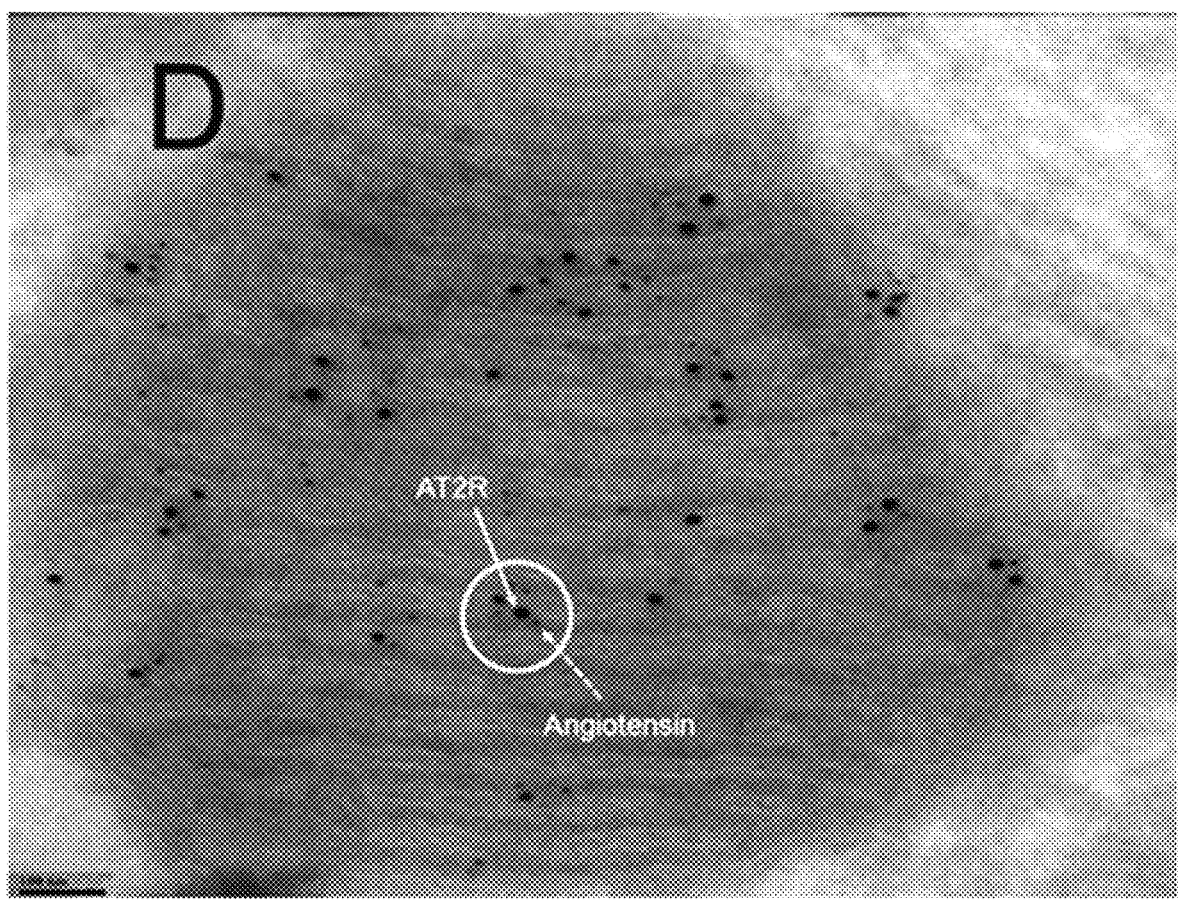

Colocalization of Ang and $AT_2Rs$. Given that a functional MAS would require the presence of local Ang to activate the receptor, we next sought evidence for mitochondrial Ang by immunoelectron microscopy. Using a gold-conjugated secondary antibody to anti-Ang antibody (6 nm gold), the presence of mitochondrial Ang was demonstrated in mouse hepatocytes (FIG. 3A), kidney tubular cells (FIG. 3B), brain neurons (FIG. 3C), and heart myocytes (FIG. 3D). Moreover, Ang was not randomly distributed within mitochondria; rather, it colocalized with mt$AT_2R$, detected with a gold-conjugated secondary antibody to anti-$AT_2R$ antibody (12 nm gold). The abundant distribution of mtAT$_2$R in the young animals, observed in electron microscope images, was correlated with a scarcity of mtAT$_1$R. Despite the observation of many Ang immunolabeled particles in electron microscope images, Ang was not detected in Western blots of isolated, density-purified mitochondria, indicating that Ang is loosely bound and is lost upon washing the isolated mitochondria.

Example 3

Figure 4:
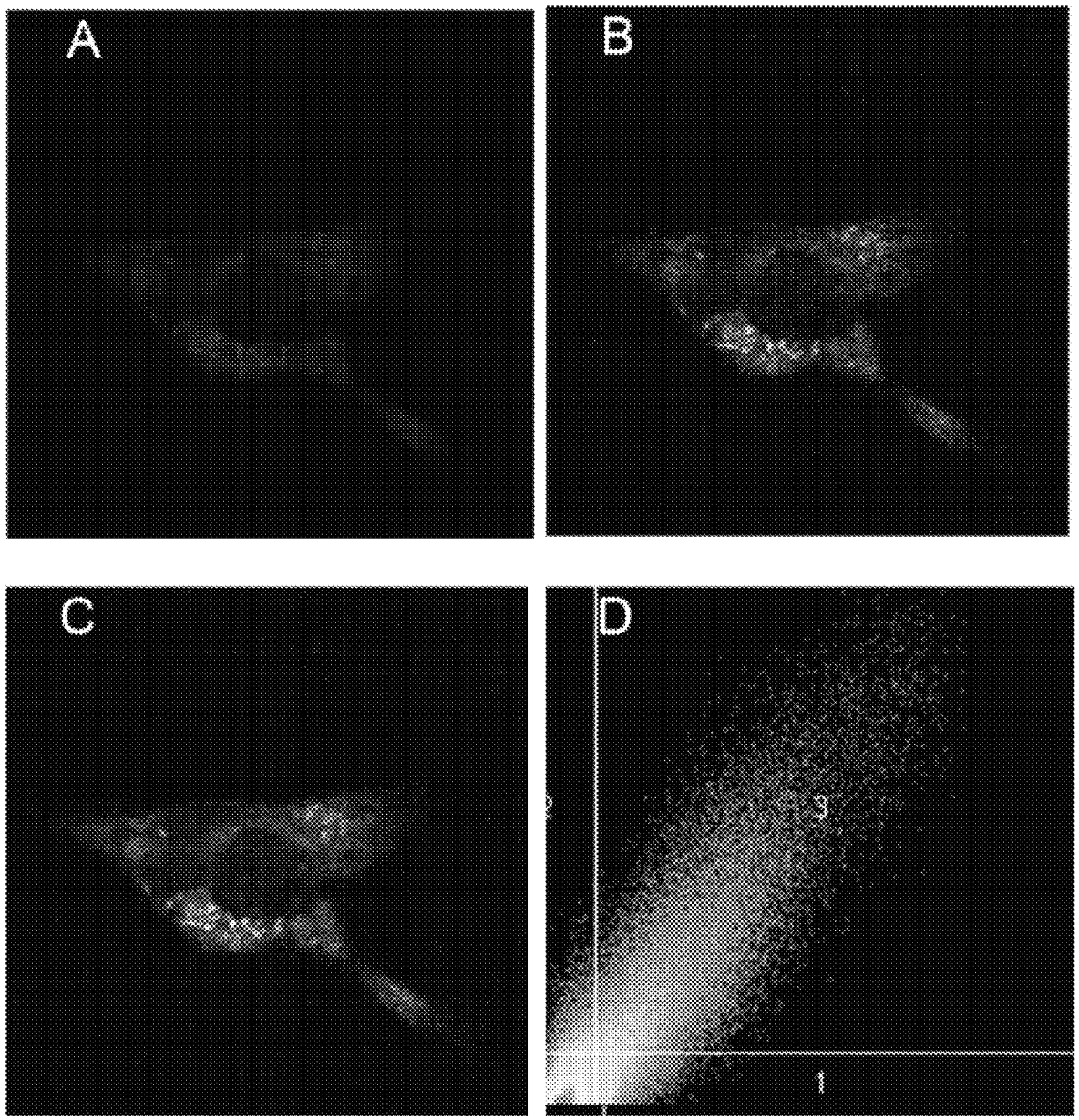
FIG. 4 are photographs showing that transfected $AT_2Rs$ colocalize with mitochondria in human fibroblasts. Human fibroblast cells were transfected with pcDNA-Cycle 3 GFP-$AT_2R$ construct (4B) or positive control using pcDNA-EGFP-Cl (4F) and counterstained with MitoTracker Red (4A and 4E) (100× oil immersion). The merged images show yellow fluorescence (4C and 4G). Fluorographic analysis (4D and 4H) reveals a high correlation coefficient ($R^2$=0.72), suggesting a strong colocalization between $AT_2Rs$ and MitoTracker within the mitochondria.
Figure 4:
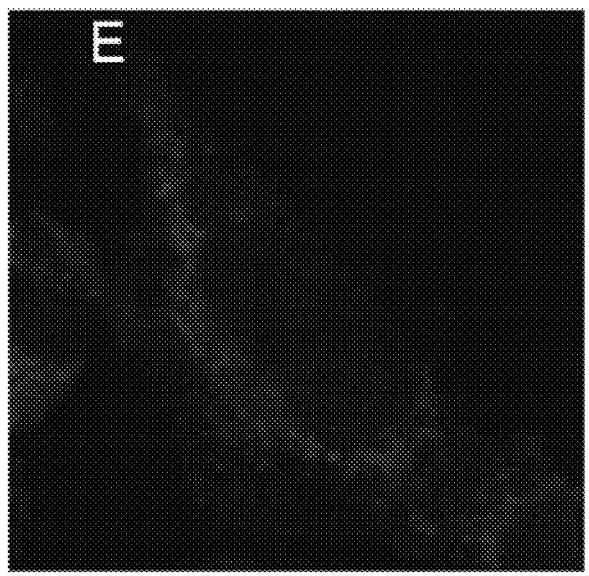
Figure 4:
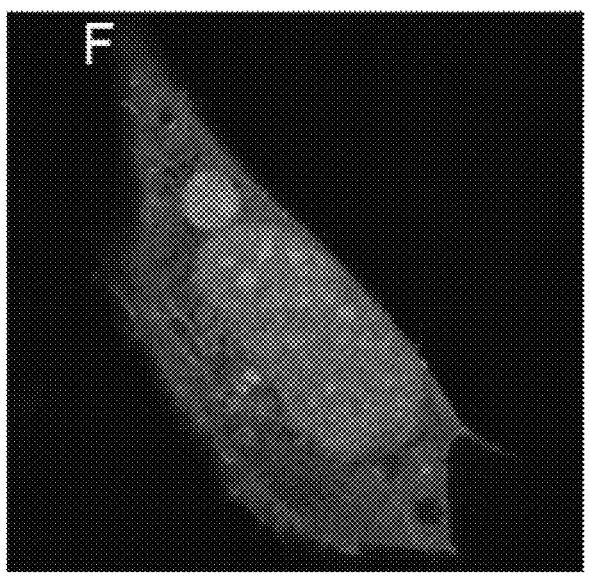
Figure 4:
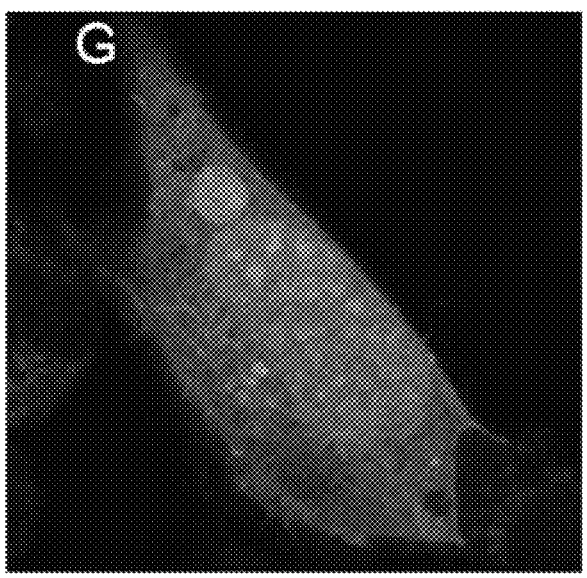
Figure 4:
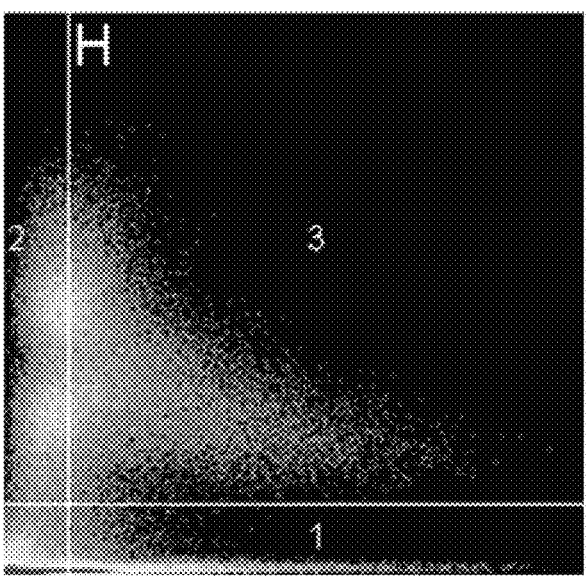

AT$_2$R Transfection of Fibroblast Cells. To ensure that the results described above were not attributable to nonspecific or off-target binding of antibody to mitochondrial targets, mitochondrial localization of AT$_2$Rs were confirmed by using a GFP-AT$_2$R fusion construct. Briefly, human fibroblasts were transfected with pcDNA-Cycle 3 GFP-AT$_2$R or positive control using pcDNA-EGFP-Cl before counterstaining with the mitochondrial fluorescence marker MitoTracker Red. GFP-AT$_2$R fluorescence was confined to discrete intracellular puncta (FIG. 4B), mirroring the distribution of MitoTracker Red (FIG. 4A). Spatial overlap of the two signals, denoting subcellular colocalization, is shown in FIG. 4C. The extent of colocalization was assessed quantitatively over a series of confocal Z sections (0.37 μm); spatial signal correlation between the two fluorophores was high ($R^2=0.72$). Thus, the high density of AT$_2$Rs observed in the mitochondria in electron microscope images was corroborated by tracking the Cycle 3 GFP-AT$_2$R fusion protein in live human fibroblasts, where it was predominantly colocalized with the mitochondrial marker MitoTracker Red.

Example 4

Figure 5:
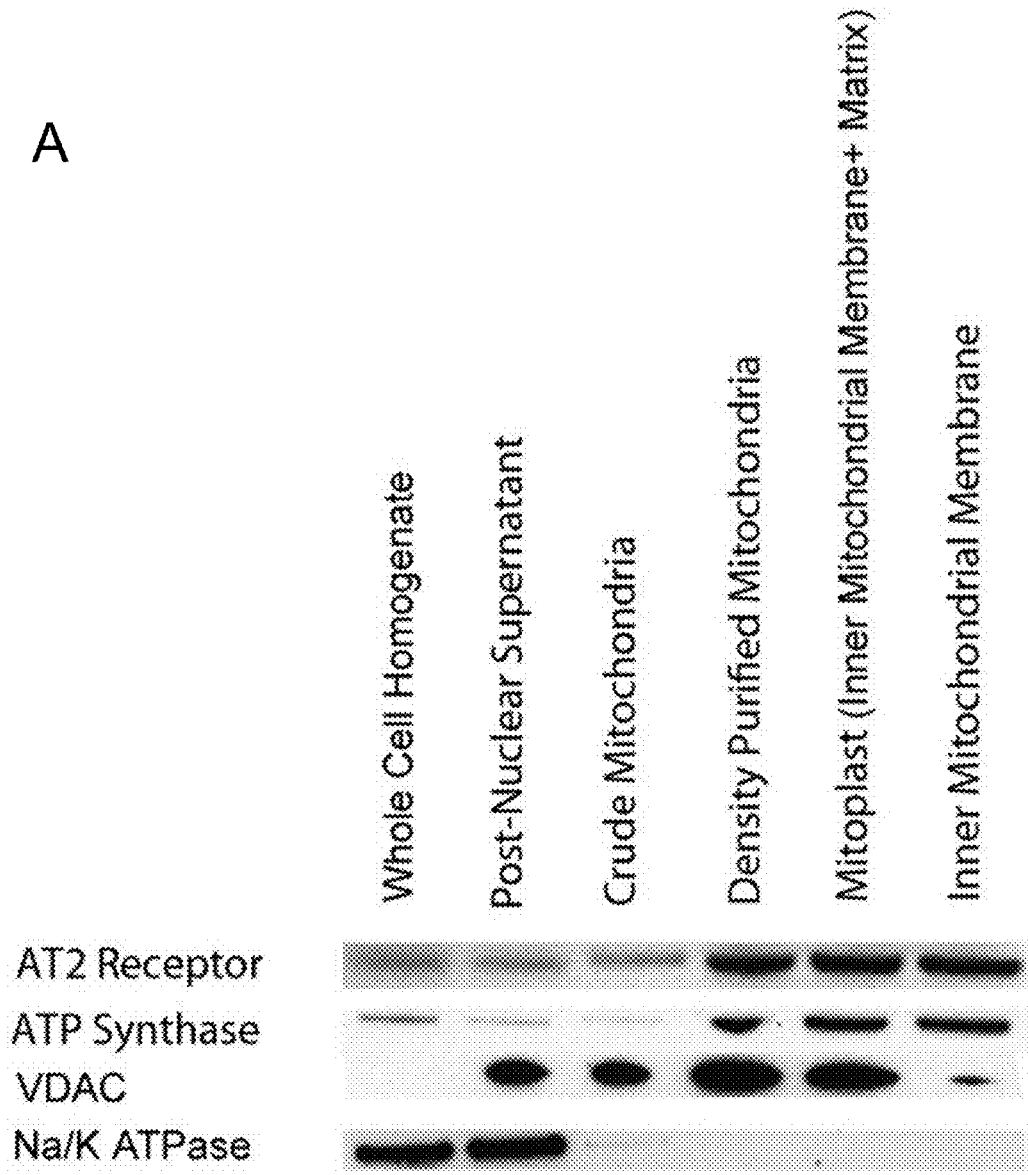
FIG. 5 is a series of graphs depicting the purification of inner mitochondrial membrane $AT_2Rs$. (5A) Whole-liver homogenate fractionations up to the inner mitochondrial membrane were subjected to 12% SDS/PAGE and immunoblotting with anti-$AT_2R$ as well as anti-$Na^+/K^+$ ATPase, anti-VDAC, and anti-ATP synthase β for detecting cell membrane, outer mitochondrial membrane, and inner mitochondrial membrane markers, respectively. $AT_2Rs$ tracked with inner mitochondrial membrane marker ATP synthase β, consistent with inner mitochondrial membrane localization of $AT_2Rs$. (5B) Integrated densitometric band analysis of immunoblots demonstrating fold enrichment of $AT_2Rs$, inner mitochondrial membrane marker (ATP synthase), outer mitochondrial membrane marker (VDAC), and plasma membrane marker (Na/K ATPase) with mitochondrial purification. (5C) Percentage enrichment of $AT_2Rs$ with cellular subfractions through mitochondrial purification. Fractions: 1, whole-cell lysate; 2, postnuclear (480×g); 3, postdifferential centrifugation (7,700×g); 4, post-HistoDenz gradient centrifugation (50,500×g); 5, postsucrose gradient centrifugation (77,000×g).
Figure 5:
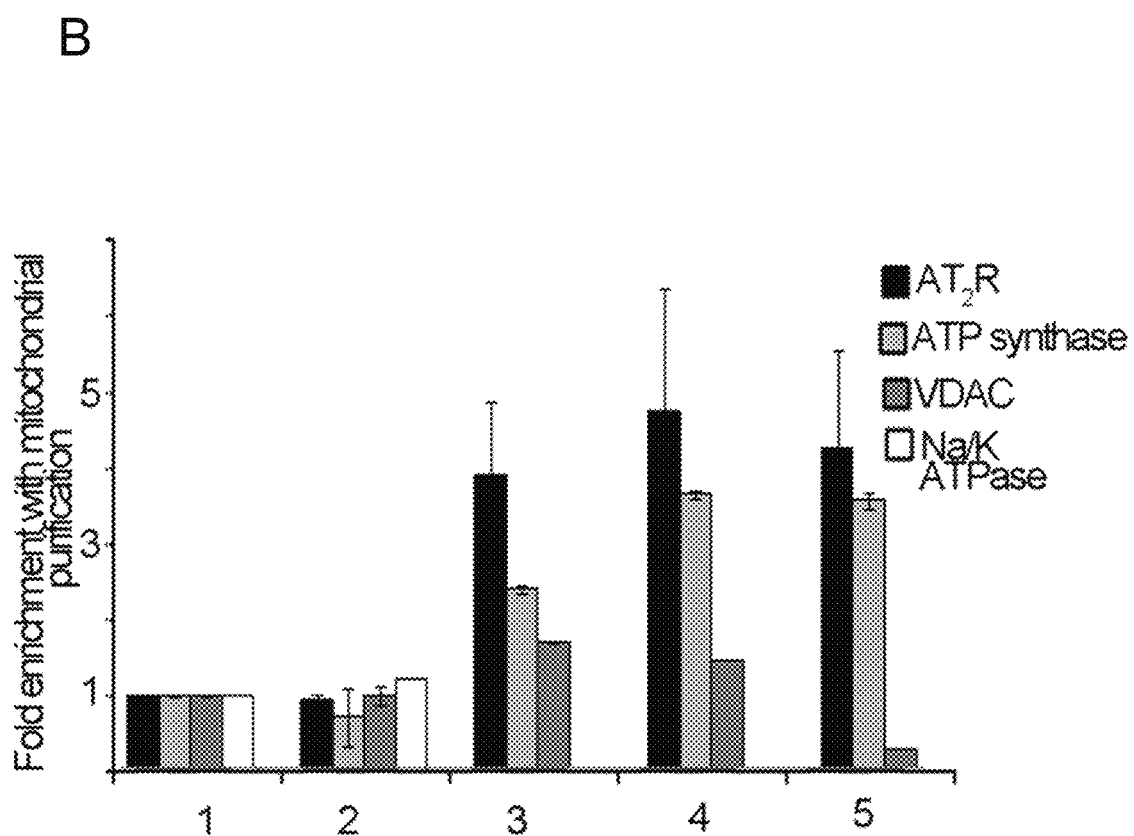
Figure 5:
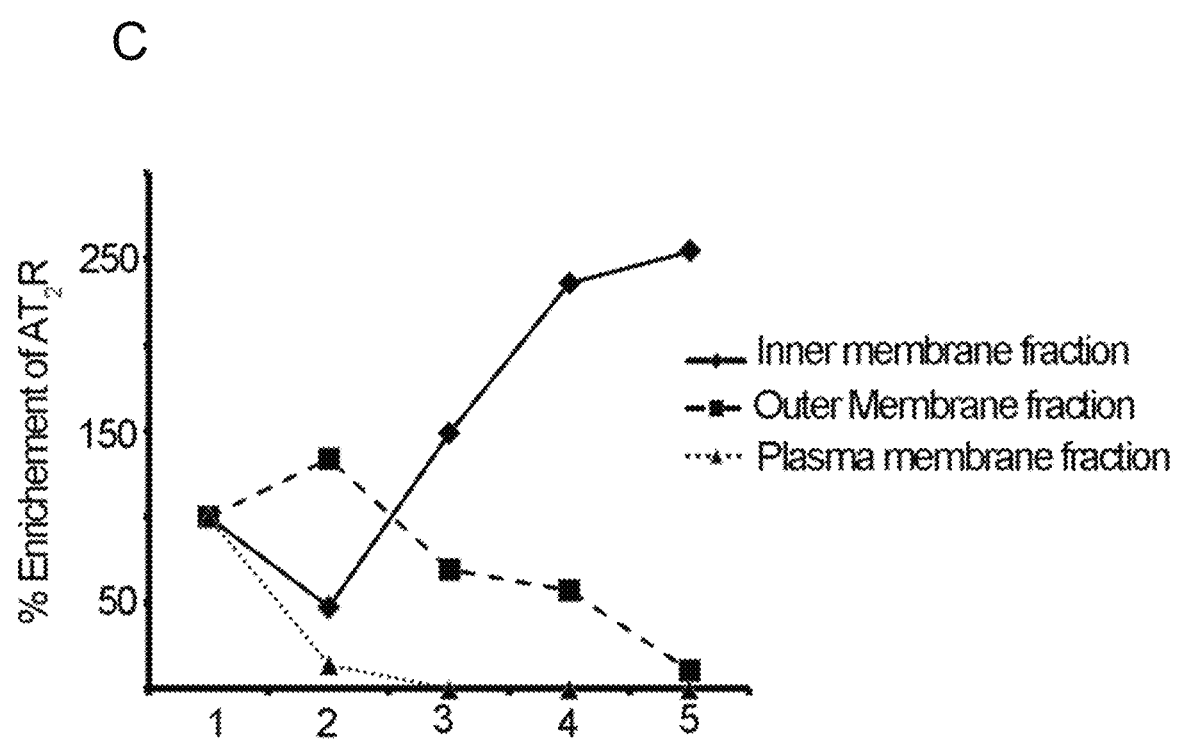

AT$_2$R Localization within Mitochondria. Having confirmed the presence of mtAT$_2$Rs by two independent methods, determination of the precise location of these receptors within the mitochondria was sought. Further inspection of the immunoelectron micrographs in FIGS. 2 and 3 suggested that the mtAT$_2$R is resident in the inner, rather than the outer, mitochondrial membranes. To confirm this observation by a different method, inner mitochondrial membrane-enriched membranes were isolated from mouse liver according to previously published methods. The specific immunoreactivity of AT$_2$R in the inner mitochondrial membrane was determined as described in the previous section. AT$_2$R immunoreactivity co-purified with that of ATP synthase β, an inner mitochondrial membrane marker. In contrast, markers of the plasma membrane (Na$^+$/K$^+$ ATPase) and the outer mitochondrial membrane [voltage-dependent anion channel (VDAC)] were progressively removed by inner mitochondrial membrane purification (FIG. 5A). These results buttress the results of the immunoelectron microscopy studies and are consistent with localization of AT$_2$R in the inner mitochondrial membrane.

Example 5

Figure 6:
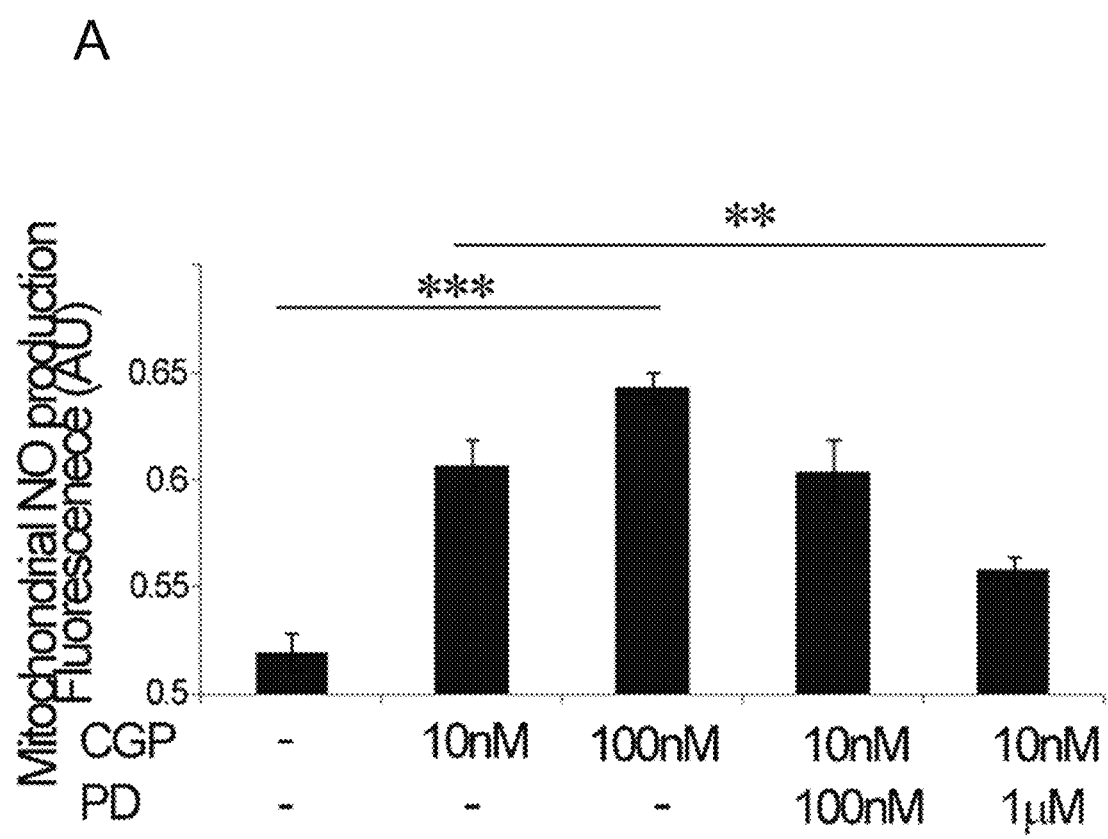
FIG. 6 is a set of 4 graphs depicting $mtAT_2R$ modulation of mitochondrial respiration and NO production. (6A) Increased mitochondrial NO production in response to 10 nM and 100 nM concentrations of the $AT_2R$ agonist CGP421140 (CGP), which can be reversed with the addition of a 1 μM concentration of the $AT_2R$ antagonist PD-123319 (PD). (6B) Mitochondrial respiration decreased significantly in response to serially increasing concentrations of CGP421140. Linear regression of CGP421140 concentrations versus oxygen consumption was significant at $P<0.0004$. (6C) Decreased respiration in response to $AT_2R$ agonist CGP421140 at 100 nM was reversed with the addition of $AT_2R$ antagonist PD-123319 at 1 μM or an inhibitor of NO production, 1-NAME, at 100 nM. (6D) No changes in mitochondrial membrane potential ($\Delta\psi_m$) are evident in response to CGP421140 at increasing concentrations, confirming that effects observed on mitochondrial respiration are not attributable to nonspecific effects of CGP421140 on mitochondrial bioenergetic parameters. (*$P<0.05$, $P<0.005$. *$P<0.0005$.)
Figure 6:
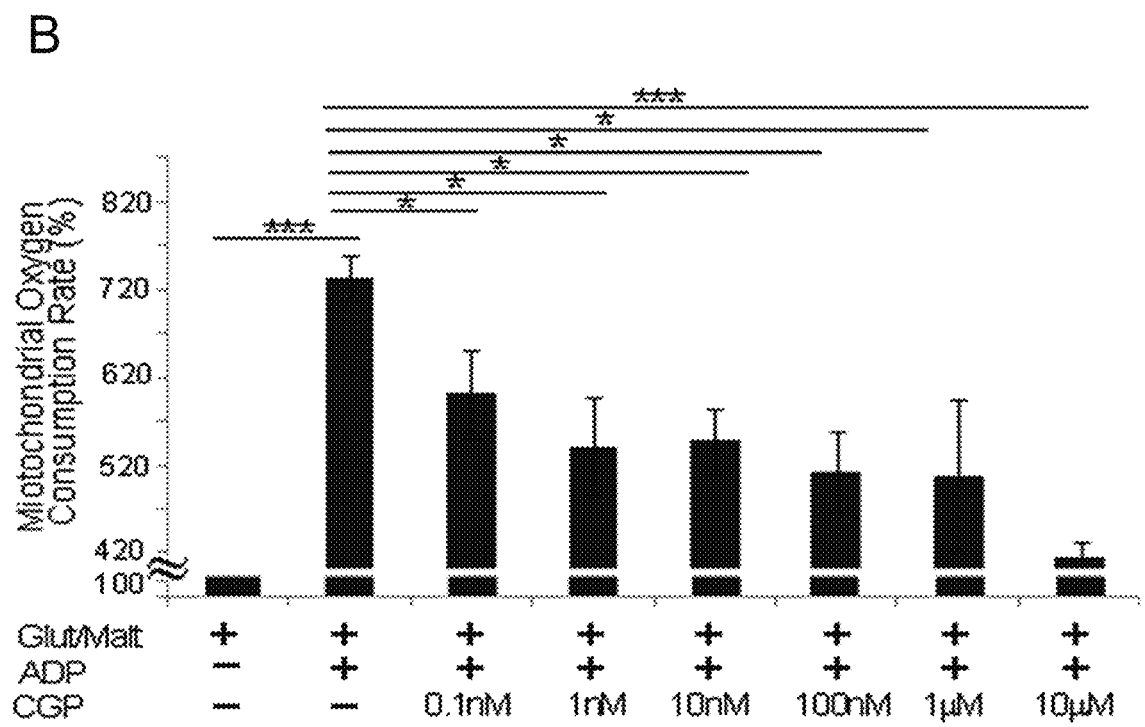
Figure 6:
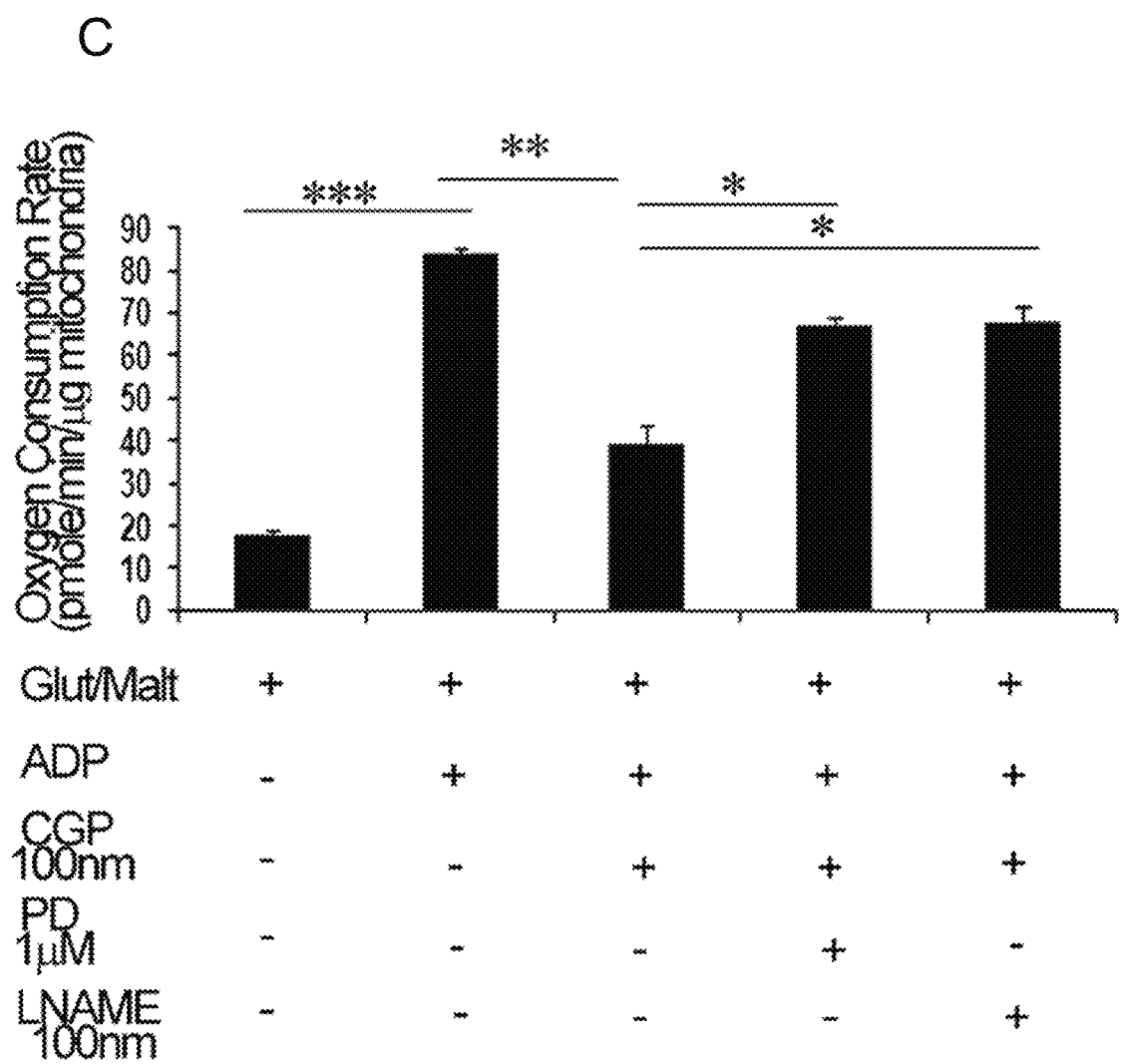
Figure 6:
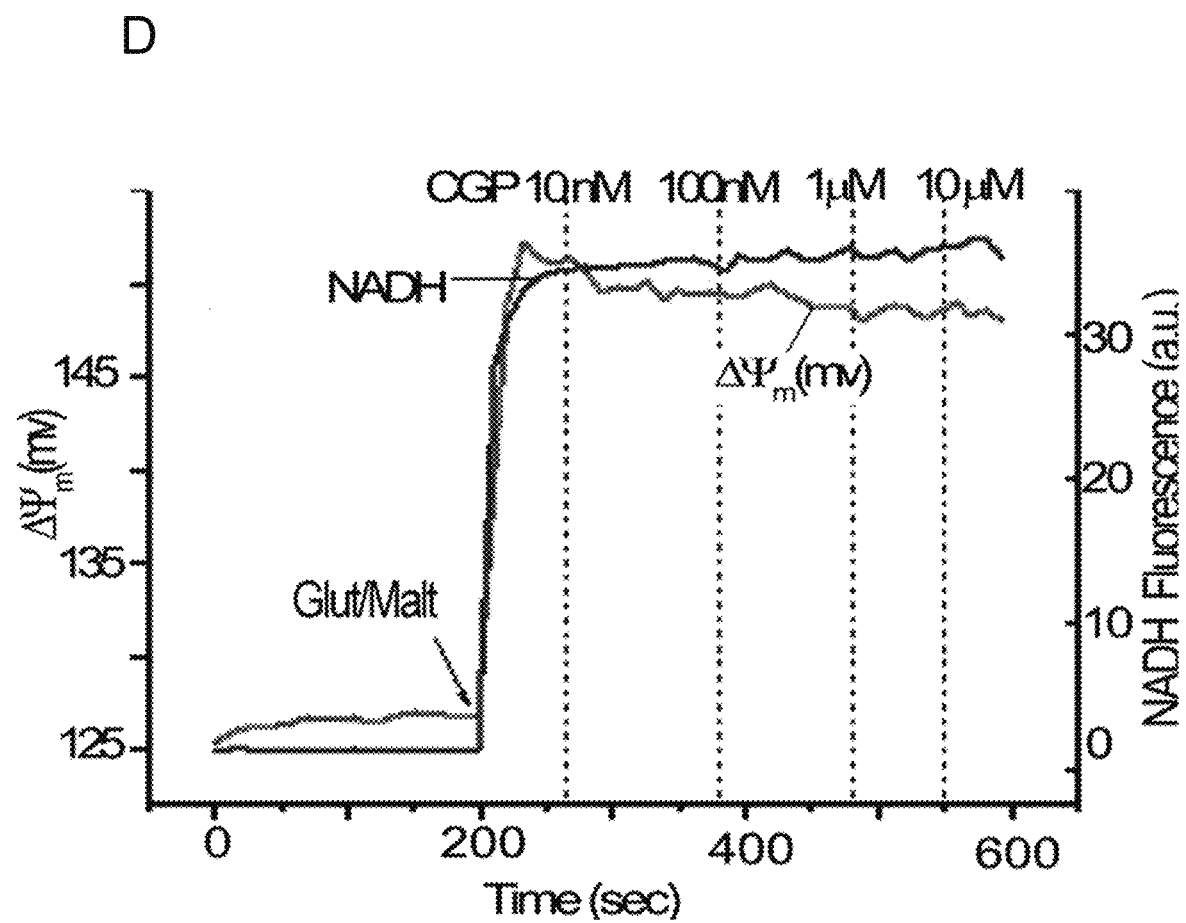

AT$_2$Rs Modulate Mitochondrial NO Production. To determine whether mtAT$_2$R activation might modulate mitochondrial NO production in a manner analogous to the actions of non-mtAT$_2$Rs on other NO isoforms, the direct effects of AT$_2$R agonists and antagonists were determined on isolated kidney mitochondria. Transmission electron microscopy and Western blot analyses were used to confirm minimal contamination of the isolated mitochondria with other cell fractions and a typical morphology of mitochondria. The NO fluorescent molecular detection probe kit (Enzo Life Sciences) was used according to the manufacturer's instructions. Isolated mitochondria were treated for 30 minutes with the NO scavenger 2-(4-carboxyphenyl)-4,4,5,5-tetramethylimidazoline-1-oxyl-3-oxide (c-PTIO) followed by a 15-min incubation with the AT$_2$R agonist CGP421140 and/ or the antagonist PD-123319. Positive control samples were treated with the NOS substrate L-arginine, and negative control samples were generated by treatment with NO scavenger (c-PTIO). Isolated mitochondria were treated and then incubated with a specific fluorescent probe for real-time measurement of NO. Fluorescence signal was measured by using a multimode microplate reader equipped with Cyanine 5 (650/670 nm). Treatment of mitochondria with CGP421140 caused a concentration-dependent increase in mitochondrial NO production (FIG. 6A); specifically, 10 nM was sufficient to stimulate NO production [from 0.52±0.0009 fluorescence arbitrary units (AU) at baseline control to 0.6+0.01 AU, $P<0.001$]. Moreover, CGP421140-stimulated NO production was mitigated by pretreatment with PD-123319 (1 μM; 0.55±0.006 AU, $P<0.01$; FIG. 6A).

Example 6

AT$_2$Rs Modulate Mitochondrial Respiration. To determine how mtAT$_2$R stimulation might influence global mitochondrial function, we examined effects on respiration in rat heart mitochondria. Glutamate/malate-supported respiration (state 2) (Nicholls D. G., et al. (2002) *Bioenergetics* 3 (*Academic, London*). 3rd Ed.) was initially 17.8±1.06 pmol/ min per μg. Addition of ADP increased respiration (state 3) to 84.12±1.24 pmol/min per Ipg ($P<0.0005$). We subsequently found that the addition of 100 nM CGP421140 caused a significant decrease in state 3 respiration (FIG. 6C; 39.47±4.37 pmol/min per μg, $P<0.005$). The dose of 100 nM CGP421140 was selected based on a series of experiments used to determine the dose of CGP421140 needed to influence mitochondrial respiration (FIG. 6B). The effects of CGP421140 were not likely attributable to nonspecific uncoupling because control experiments showed that 100 nM CGP421140 had little effect on mitochondrial membrane potential ($\Delta\psi_m$) or NADH level (FIG. 6D). Importantly, CGP421140-mediated inhibition of respiration was prevented by blocking the AT$_2$R; PD-123319 (1 μM) restored CGP421140-inhibited state 3 respiration (FIG. 6C; 66.83±2.1 pmol/min per μg, $P<0.01$). The addition of L-N$^G$-nitroarginine methyl ester (L-NAME; 1 μM), an arginine analog that inhibits NO production, reversed the CGP421140 effect on mitochondrial respiration (FIG. 6C; 67.4±4.3 pmol/min per μg, $P<0.05$), indicating that the functional effects of mtAT$_2$R activation on mitochondrial respiration are via an NO-dependent mechanism.

To further validate this effect of MAS on mitochondrial respiration, we studied liver mitochondria with different mitochondrial substrates. Liver mitochondria respiring with glutamate/malate as the substrate gave results similar to those obtained in isolated cardiac mitochondria. The AT$_2$R agonist inhibited state 3 respirations in the nanomolar range for both glutamate/malate- and succinate-supported respiration. In succinate-supported respiration, the inhibitory response was slightly more pronounced at 1 nM than for glutamate/malate-supported respiration (data not shown).

Example 7

Figure 7:
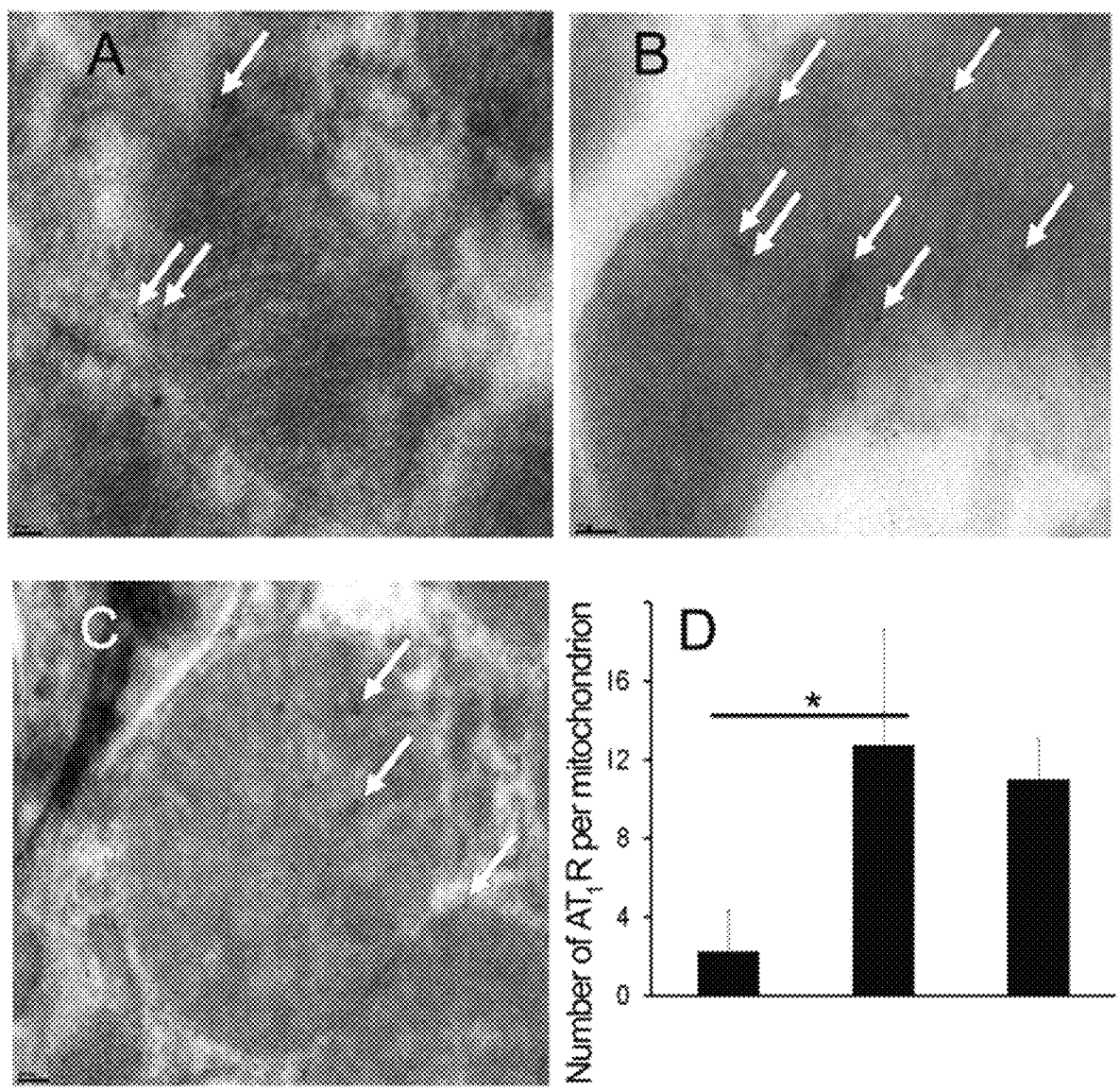
FIG. 7 are photographs and graphs depicts the effect of $AT_1R$ antagonist losartan on expression of mitochondrial $AT_1Rs$ and $AT_2Rs$. Renal tubular cell sections from C57BL/6 20 wks old (7A and 7E), 70 wks old (7B and 7F), and 70 wks old treated with losartan 40-60 mg/kg/day for 20 wks (7C and 7G). 7D and 7H represent average counts of immune-labeling densities of $mtAT_1R$ (7D) and $mntAT_2R$ (7H) by age group in response to losartan. Gold particles in 30 mitochondria from each immunolabeling experiment were counted and averaged. Age was associated with a significant decrease in $mtAT_2R$ that was reversed with chronic use of losartan. *$P<0.005$, **$P<0.0005$.
Figure 7:
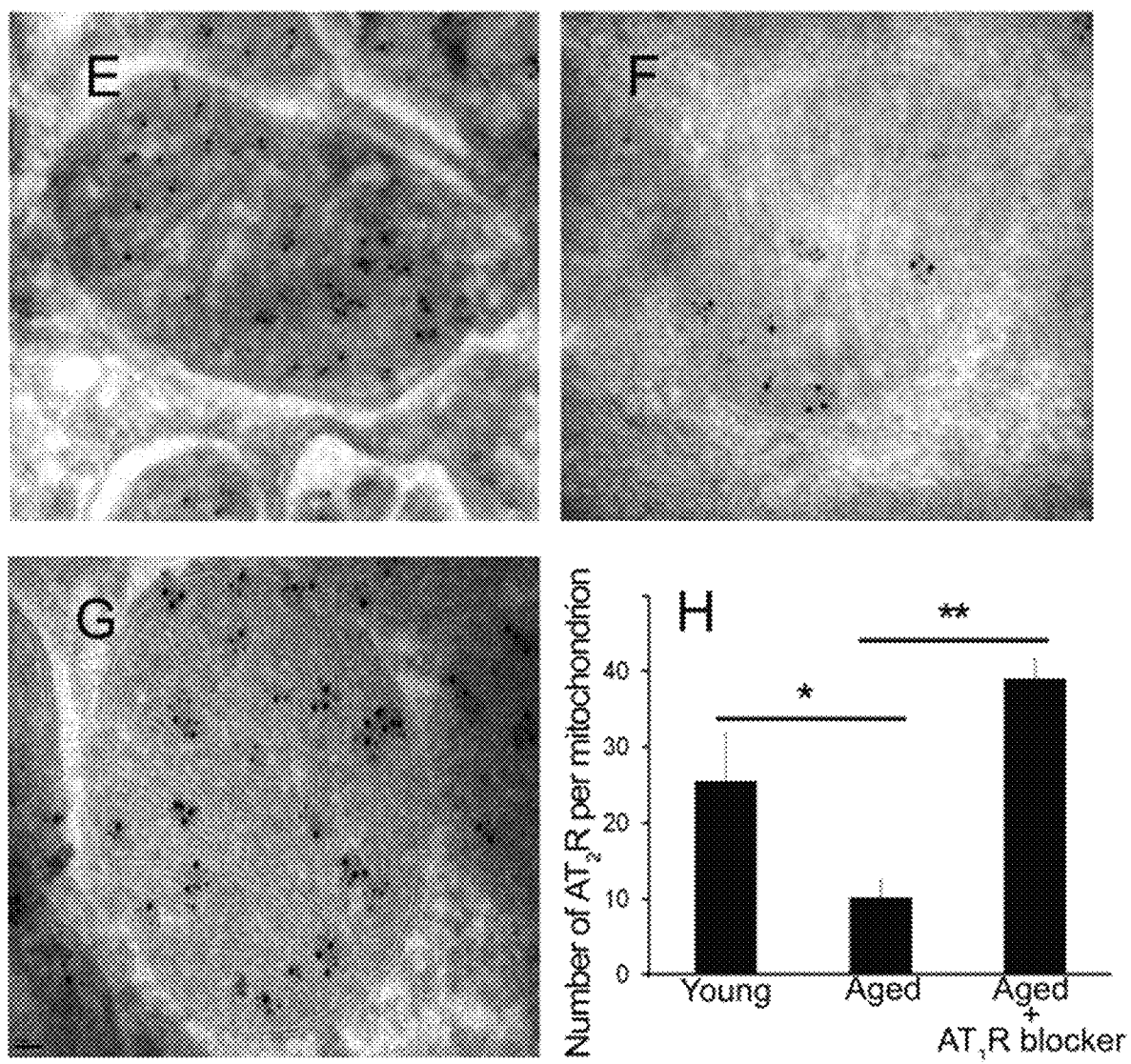

Age-Related Changes in the MAS. The effect of aging on the MAS was examined. Kidney tubular cell sections from 20- or 70-wk-old C57BL/6 mice and aged (70-wk-old) mice treated with losartan at a dose of 40-60 mg/kg per day for 20 wk were labeled with antibodies and visualized with immunoelectron microscopy. Representative mitochondria, labeled for $AT_1R$ (FIGS. 7A-C) and $AT_2R$ (FIGS. 7D-F) are shown. Younger mice (FIGS. 7A and 7D) and older mice treated with losartan (FIGS. 7C and 7F) had similar densities of labeled $AT_2R$, whereas older untreated mice (FIGS. 7B and 7E) had a lower $AT_2R$ density. Our results demonstrate a significant decrease in the expression of $mtAT_2R$ with aging (from 25.5+6.2 to 10.2+2.2 gold-labeled $AT_2R$ per mitochondrion, P<0.001) that is reversed by treatment with losartan (39.0+2.6 gold-labeled $AT_2R$ per mitochondrion). In contrast, $mtAT_1R$ was significantly increased with aging (from 2.0+2.2 to 12.7+5.8 gold-labeled $AT_1R$ per mitochondrion, P<0.001). This increase was slightly attenuated with chronic $AT_1R$ blockade (11.0+2.1 gold-labeled $AT_1R$ per mitochondrion).

Example 8

For wound-healing experiments, animal procedures were approved by the Johns Hopkins University Animal Care and Use Committee. During the experiments the animals were-housed one per cage, maintained under controlled environmental conditions (12 hours light to dark cycle, temperature approximately 23° C.), and provided with standard laboratory food and water ad libitum. 16 male mice with average weight of 30 g were divided into two groups. Mice were anesthetized with ketamine hydrochloride (100 mg/kg) and xylazine (10 mg/kg), and the dorsum was shaved and then treated with a depilatory (Nair cream, Church & Dwight Co., Princeton, N.J.). Two symmetrical full thickness excisional wounds created on their back using an 8-mm punch biopsy instrument. No dressing was used after burn. The animals were resuscitated according to the Parkland formula (4 mL/kg/percent body area) by intraperitoneal injection of saline within 1 hour after wound. Animals were divided into two groups; A and B. One group received daily application of an angiotensin receptor blocker cream to both wounds per animal and the other received vehicle. Researchers were blinded to the identity of the cream applied. We used digital photography and computerized planimetry to assess the rate of wound healing in either group.

Figure 8:
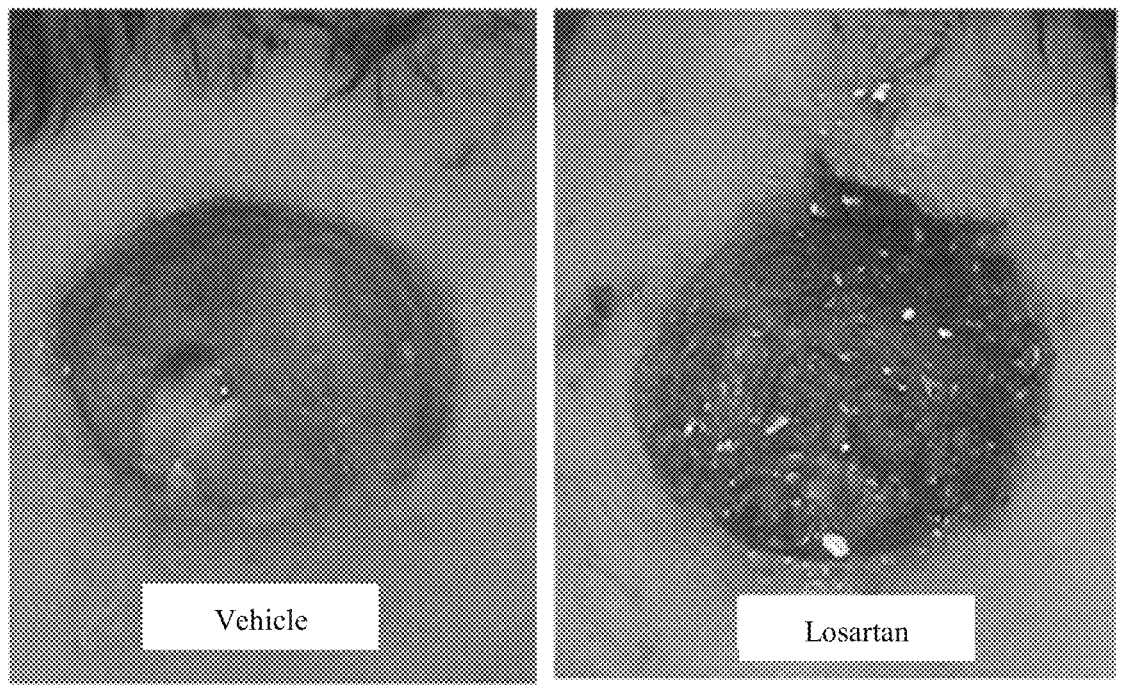
FIG. 8 includes a pair of photographs showing that the wounds in the mice treated with losartan showed more granulation than those treated with vehicle after three days of treatment.
Figure 9:
FIG. 9 includes a pair of photographs showing the difference in healing between the losartan treated mice (A) and the vehicle treated mice (B).
Figure 10:
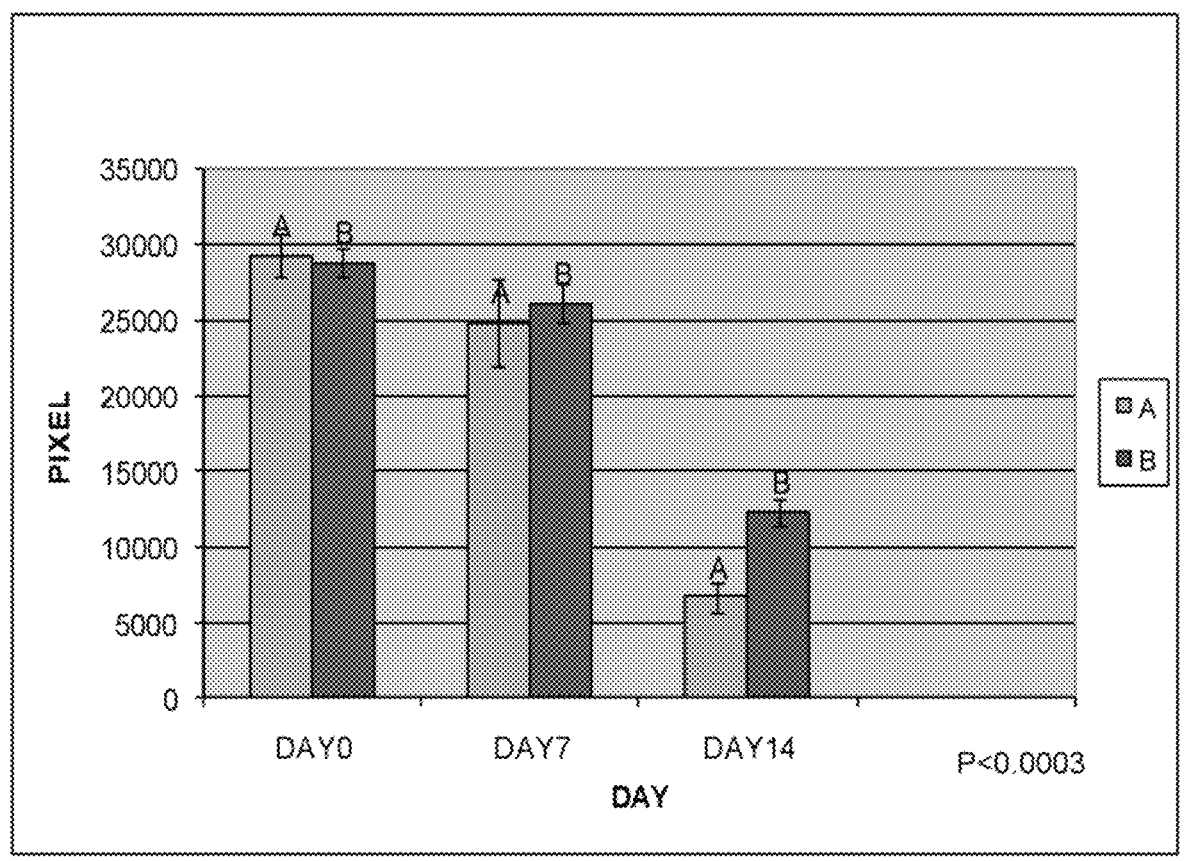
FIG. 10 is a graph of the digital photography and computerized planimetry data of the wounds in both groups (FIG. 10).

As shown in FIG. 8, the wounds in the mice treated with losartan showed more granulation than those treated with vehicle after three days of treatment. FIG. 9 also shows the difference in healing between the losartan treated mice (A) and the vehicle treated mice (B) which was corroborated by the digital photography and computerized planimetry data of the wounds in both groups (FIG. 10).

Example 9

Some studies have demonstrated that stimulating Ang II receptors in the first 4 days of after wounding may accelerate wound healing through amplification of inflammatory and early proliferative signaling. However, more recent evidence suggests that high levels of Ang II (high RAS activity) are already present in wound tissue and that this is associated with healing abnormalities. Indeed, the ratio of proinflammatory $AT_1R$ to anti-inflammatory $AT_2R$ are dysregulated in both aging and diabetes, and our evidence shows that losartan improves this ratio. This suggests that the early phase RAS pro-inflammatory signaling may be higher and may continue into later healing phases, which in turn may slow wound healing. Hence, it was hypothesized that blocking $AT_1R$ (and hence RAS) signaling with losartan during the proliferative/remodeling phase (day 7+) rather than earlier phases would facilitate wound healing.

Figure 11:
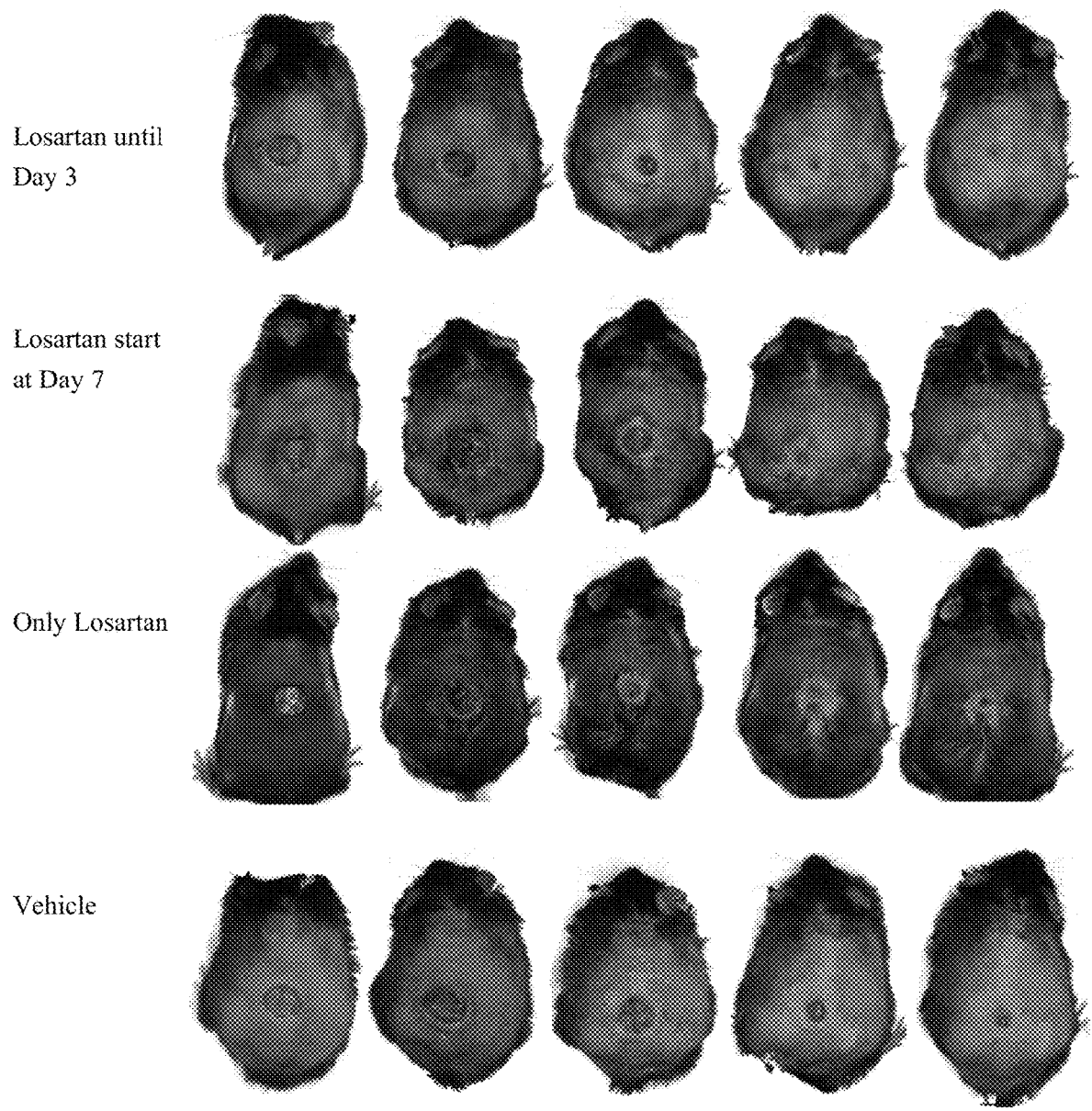
FIG. 11 comprises images of representative dbdb mice from 3 and treatment groups and control on days 0, 6, 9, 13, and 16 post-treatment.
Figure 12:
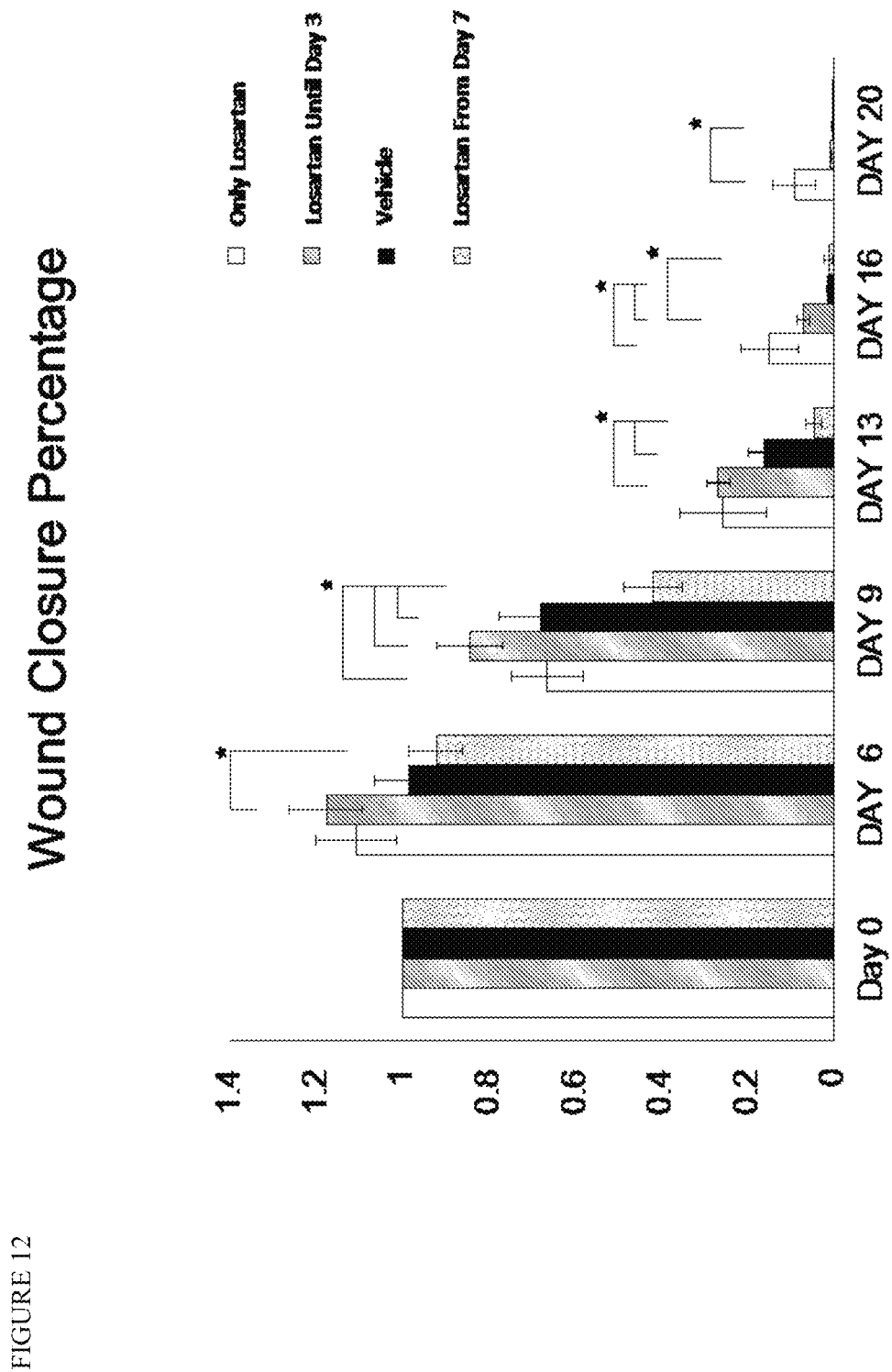
FIG. 12 depicts graphs showing percent wound closure from 3 treatment groups and control across treatment period (n=9 each group) showing significant acceleration in % closed in group 2 by day 9, 13 and 16 (*$p<0.05$).
Figure 13:
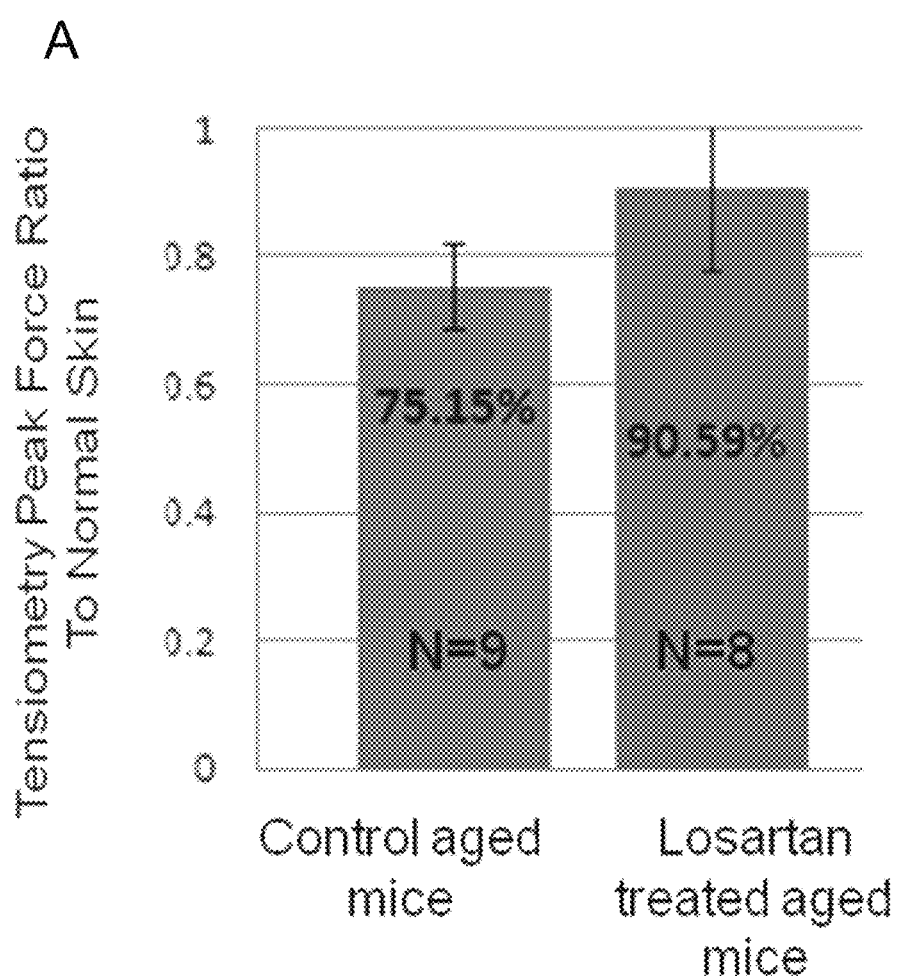
FIG. 13 are graphs depicting the effects of 10% topical losartan compared to placebo control in 20 month old mice on A) peak force needed to break healed skin at day 20 after wounding, B) elasticity ratio of skin after treatment, C) blood flow to the wounds by Doppler at day 10 after wounding and D) the average time to wound closure. Results showed that the treatment group healed significantly faster (approximately 2 days earlier, $p<0.05$), had significantly increased blood flow to wound (p=01), and had more elasticity in healed tissue as compared to the age-matched placebo control.
Figure 13:
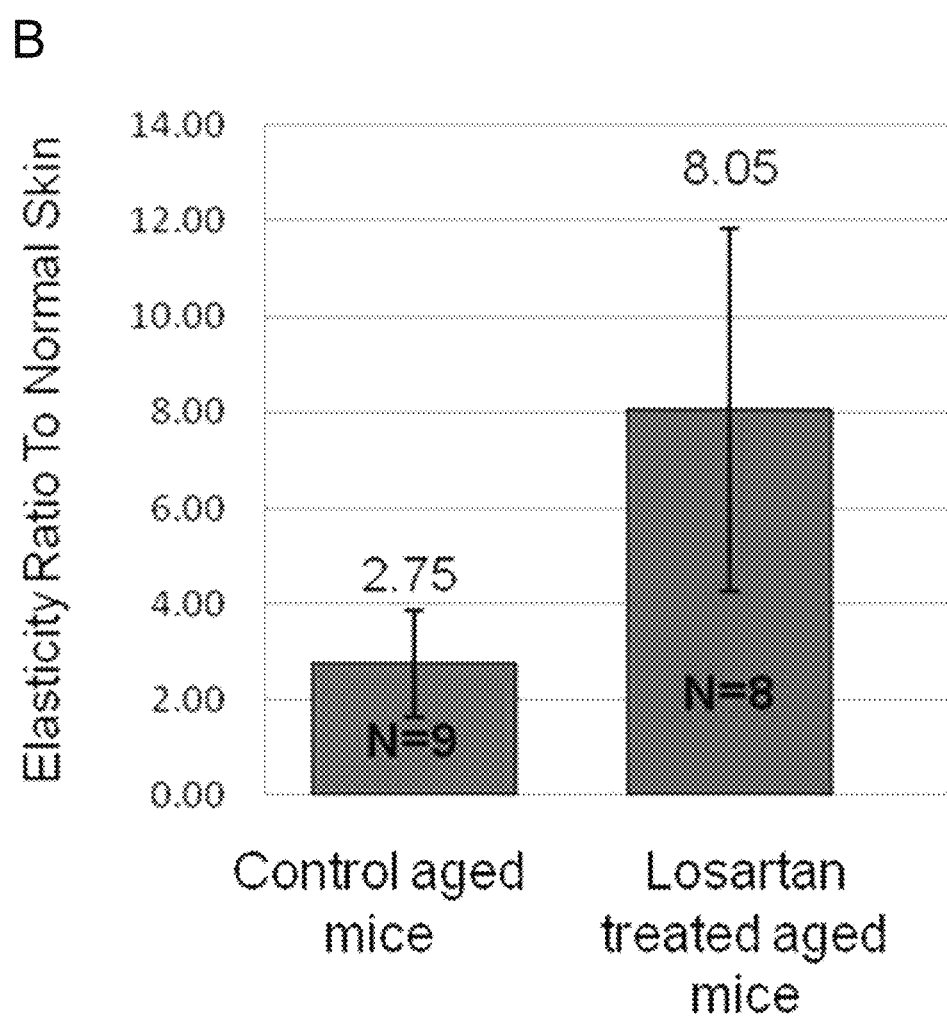
Figure 13:
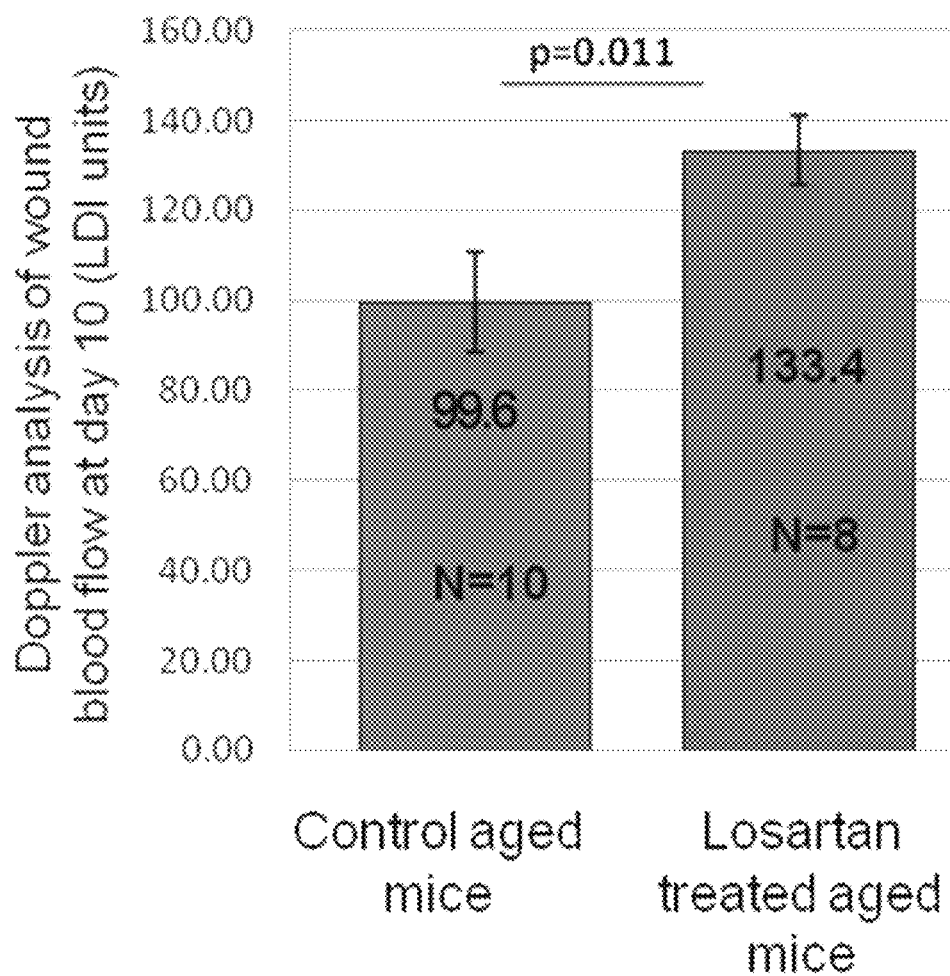
Figure 13:
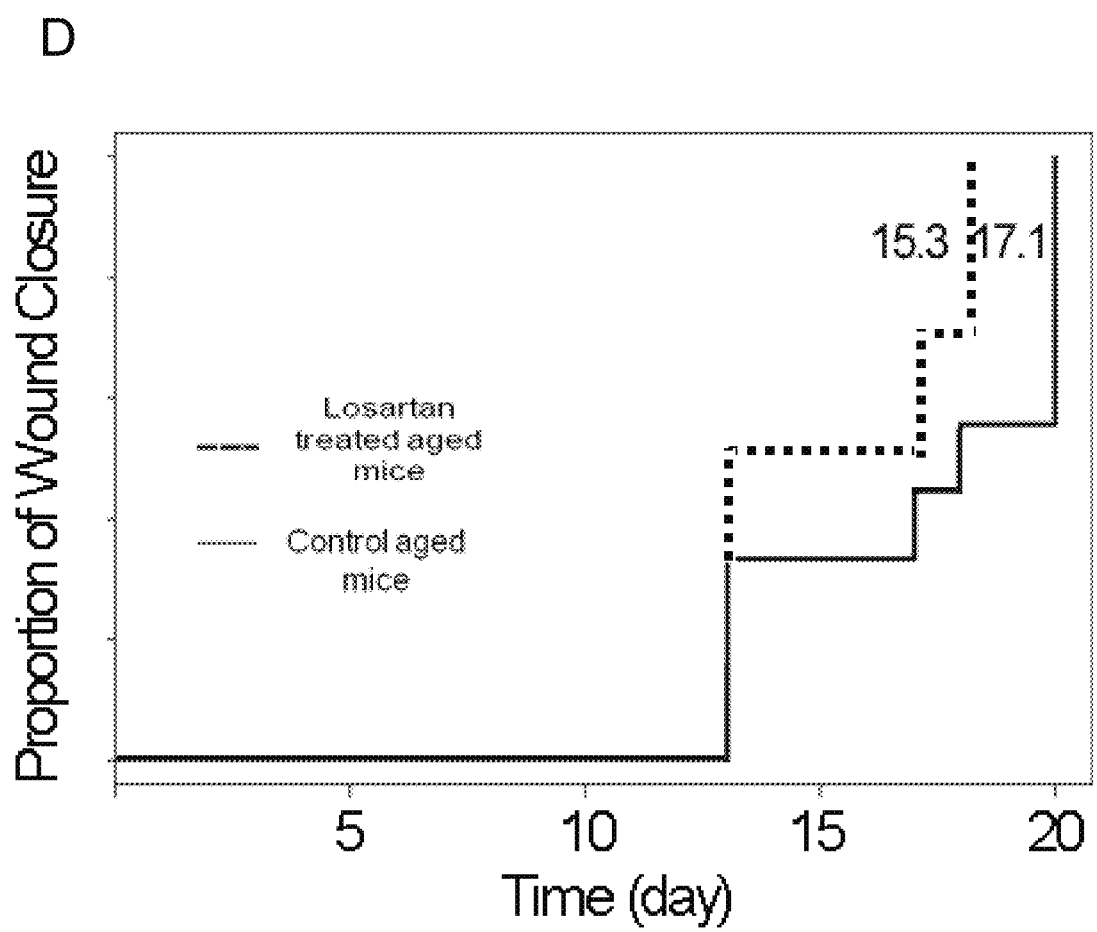

In order to provide additional rationale for using losartan ointment at day 7 of wound treatment, preliminary data was developed on the effects of losartan on all phases of wound healing in 8 week old BKS.Cg-m+/+Lepr$^{db}$/J(db/db) mice (FIGS. 11, 12). These results show accelerated healing and improved elasticity in those mice treated starting at day 7 compared to those treated with losartan starting at day 1. This provided important rationale for testing losartan at day 7 in wound healing in an aging mouse model. For preliminary aging studies, we divided C57B1/6 male mice aged 2 and 20 months into control and treatment groups, generated 8 mm dorsal wounds, and applied 10% losartan ointment to treatment group starting at day 7. Dosing was extrapolated from that found to be effective in skeletal muscle healing. As expected, the results suggest that younger animals heal significantly faster than older animals (data not shown). The older animals treated with 10% losartan ointment starting at day 7 after wounding have significantly shorter time to closure, more blood flow to the wound at day 10, and increased elasticity of the healed skin compared to the aging control group and the end of treatment (FIG. 13). Although these data are not conclusive, they support our hypothesis, allowed the optimization of the experimental design for the proposed study, and provide strong rationale to further study losartan starting at day 7 of wound healing.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having." "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating an open wound in a mammal, comprising administering to the mammal a topical dermal pharmaceutical composition; wherein The topical dermal pharmaceutical composition comprises at least one angiotensin II type 1 receptor (AT1R) antagonist selected from losartan, valsartan, telmisartan, irbesartan, olmesartan, candesartan, and eprosartan, or a salt thereof, and a pharmaceutically acceptable carrier;

the composition comprises 1-10% of the at least one angiotensin II type 1 receptor (AT1R) antagonist;

the step of administering the composition comprises topically applying the composition to the open wound; and the step of administering the composition begins 3 or more days after the mammal is wounded.

2. The method of claim 1, wherein the open wound comprises injured, scarred, or damaged skin, subcutaneous tissue, or skeletal muscle areas.

3. The method of claim 1, wherein the open wound is acne.

4. The method of claim 1, wherein the open wound is a burn or thermal injury.

5. The method of claim 1, wherein the open wound is an aging-related wound.

6. The method of claim 1, wherein the open wound is a diabetic ulcer.

7. The method of claim 1, wherein the open wound is a chronic wound.

8. The method of claim 1, wherein the topical dermal pharmaceutical is a liquid or a gel.

9. A method for treating an open wound in a mammal, comprising administering to the mammal a topical dermal pharmaceutical composition; wherein The topical dermal pharmaceutical composition comprises at least one angiotensin II type 1 receptor (AT1R) antagonist selected from losartan, valsartan, telmisartan, irbesartan, olmesartan, candesartan, and eprosartan, or a salt thereof, and a pharmaceutically acceptable carrier;

the composition comprises 1-10% of the at least one angiotensin II type 1 receptor (AT1R) antagonist;

the step of administering the composition comprises topically applying the composition to the open wound;

the step of administering the composition begins 3 or more days after the mammal is wounded; and the open wound is a diabetic ulcer.

10. A method for treating an open wound in a mammal, comprising administering to the mammal a topical dermal pharmaceutical composition; wherein The topical dermal pharmaceutical composition comprises at least one angiotensin II type 1 receptor (AT1R) antagonist selected from losartan, valsartan, telmisartan, irbesartan, olmesartan, candesartan, and eprosartan, or a salt thereof, and a pharmaceutically acceptable carrier;

the composition comprises 1-10% of the at least one angiotensin II type 1 receptor (AT1R) antagonist;

the step of administering the composition comprises topically applying the composition to the open wound;

the step of administering the composition begins 3 or more days after the mammal is wounded; and the open wound is a chronic wound.

* * * * *